United States Patent
Gadge et al.

(10) Patent No.: US 12,365,649 B2
(45) Date of Patent: Jul. 22, 2025

(54) PROCESS FOR THE PREPARATION OF BRIVARACETAM

(71) Applicant: Alivus Life Sciences Limited, Solapur (IN)

(72) Inventors: Sandip Tukaram Gadge, Navi Mumbai (IN); Shrikant Prabhakar Keshav, Panvel (IN); Nandkumar Gaikwad, Navi Mumbai (IN); Rajendra Jagdhane, Pune (IN); Sharad Gore, Kalyan (IN); Ganesh Bhaskar Chaudhari, Karjat (IN); Bhavin Prabhudas Thanki, Junagadh (IN); Suresh Kadam, Thane (IN); Shekhar Bhaskar Bhirud, Thane (IN); Venkata Raghavendra Acharyulu Palle, Mumbai (IN)

(73) Assignee: Alivus Life Sciences Limited (IN)

( * ) Notice: Subject to any disclaimer, the term of this patent is extended or adjusted under 35 U.S.C. 154(b) by 25 days.

(21) Appl. No.: 17/785,586

(22) PCT Filed: Dec. 14, 2020

(86) PCT No.: PCT/IB2020/061884
§ 371 (c)(1),
(2) Date: Jun. 15, 2022

(87) PCT Pub. No.: WO2021/124066
PCT Pub. Date: Jun. 24, 2021

(65) Prior Publication Data
US 2024/0010618 A1    Jan. 11, 2024

(30) Foreign Application Priority Data
Dec. 20, 2019   (IN) .............................. 201921053171

(51) Int. Cl.
*C07D 207/12*    (2006.01)
*A61K 9/48*    (2006.01)
*A61K 31/22*    (2006.01)
*B01J 23/40*    (2006.01)
*B01J 23/755*    (2006.01)
*B01J 27/24*    (2006.01)

(52) U.S. Cl.
CPC .......... *C07D 207/12* (2013.01); *A61K 9/4808* (2013.01); *A61K 9/4858* (2013.01); *A61K 31/22* (2013.01); *B01J 23/40* (2013.01); *B01J 23/755* (2013.01); *B01J 27/24* (2013.01); *C07B 2200/07* (2013.01)

(58) Field of Classification Search
CPC ....... C07D 207/12; B01J 23/40; B01J 23/755; B01J 27/24
See application file for complete search history.

(56) References Cited

U.S. PATENT DOCUMENTS 10,781,170 B1 *   9/2020   Divi ..................... C07D 207/12
2018/0155284 A1   6/2018   Wang et al.

FOREIGN PATENT DOCUMENTS

| CN | 105646319 B | 5/2018 |
| WO | 2016191435 A1 | 12/2016 |
| WO | 2019087172 A1 | 5/2019 |

OTHER PUBLICATIONS

Arun A. Narine, "Design, Synthesis and Evaluation of Chiral Auxiliaries, Ligands, and Catalysts for Asymmetric Synthesis," Doctoral Thesis, Simon Fraser University, Aug. 2004, pp. 4-5.

* cited by examiner

*Primary Examiner* — Sikarl A Witherspoon
(74) *Attorney, Agent, or Firm* — Michael E. Carmen

(57) ABSTRACT

The present invention relates to a process for the preparation of brivaracetam, a compound of formula I and salts thereof. The present invention also relates to a compound of formula II and a compound of formula IIA, process for its preparation and conversion thereof to brivaracetam, the compound of formula I.

20 Claims, 5 Drawing Sheets

PROCESS FOR THE PREPARATION OF BRIVARACETAM

PRIORITY

Figure 1:
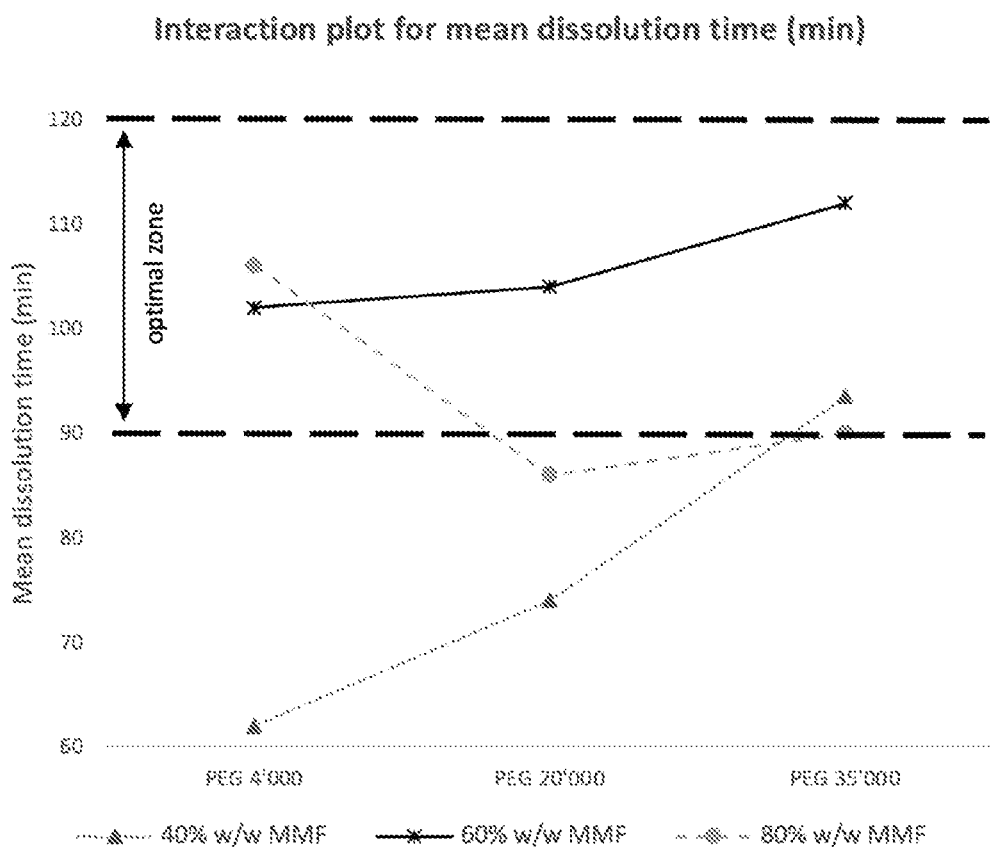
Figure 2:
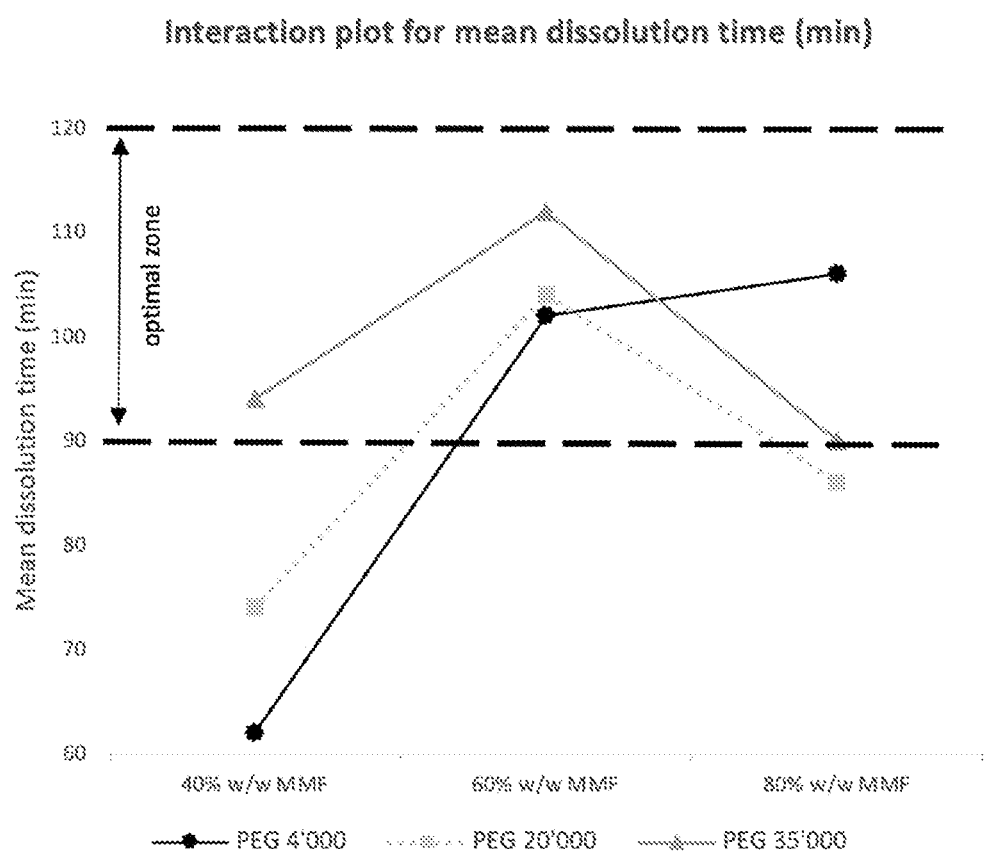
Figure 3:
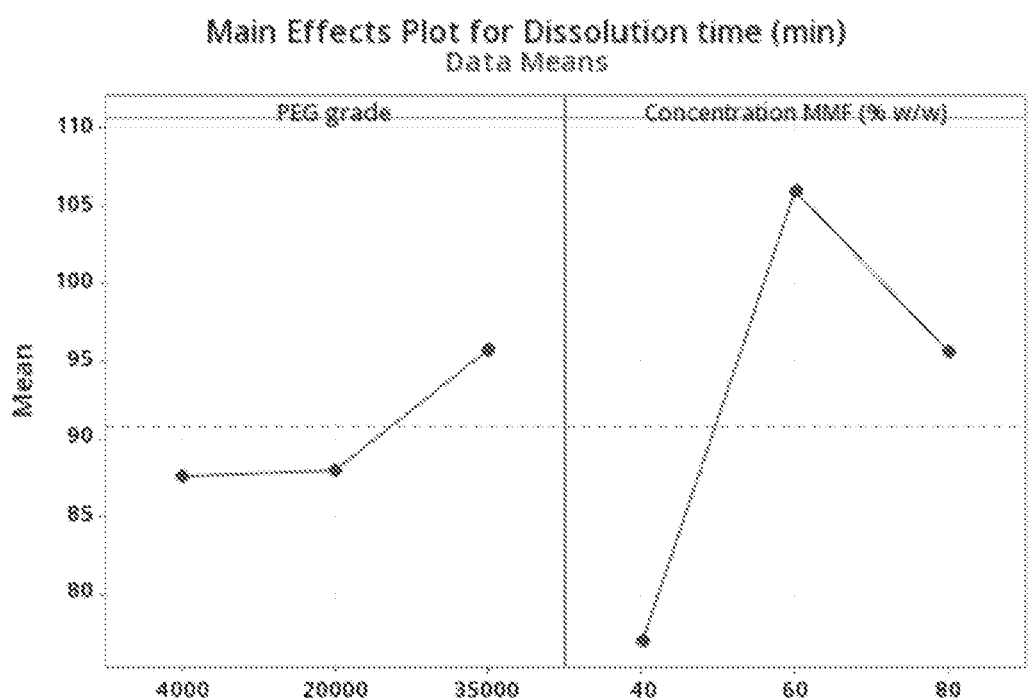
Figure 4:
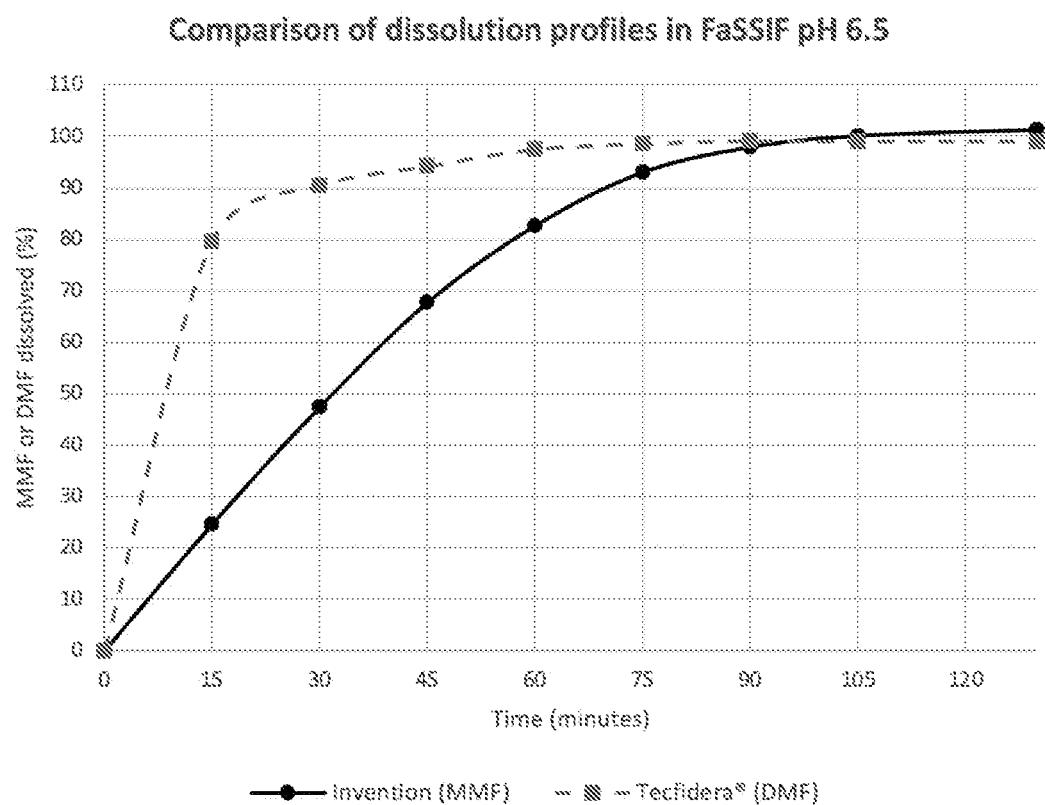
Figure 5:
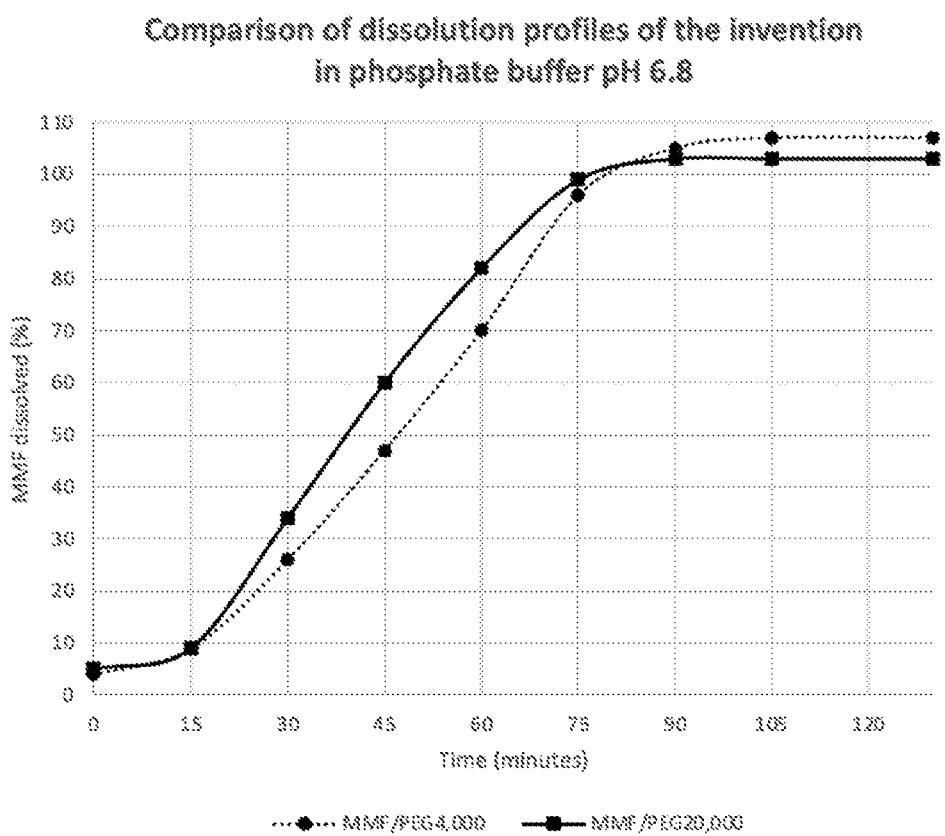

This application claims priority under 35 U.S.C. § 371 to International Application No. PCT/IB2020/061884, filed Dec. 14, 2020, which claims the benefit of Indian Provisional Application No. 201921053171, filed on Dec. 20, 2019, and entitled "PROCESS FOR THE PREPARATION OF BRIVARACETAM", the contents of which are incorporated herein by reference.

BACKGROUND OF THE INVENTION

Technical Field

The present invention relates to a process for the preparation of brivaracetam and salts thereof.

Description of the Related Art

The chemical name of BRIVIACT (brivaracetam) is (2S)-2-[(4R)-2-oxo-4-propyltetrahydro-1H-pyrrol-1-yl] butanamide, depicted by compound of formula I.

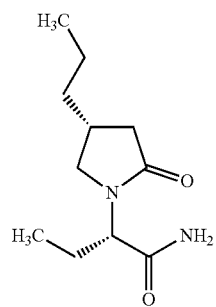

BRIVIACT® is indicated as adjunctive therapy in the treatment of partial-onset seizures in patients 16 years of age and older with epilepsy. BRIVIACT® is available as 10 mg, 25 mg, 50 mg, 75 mg, and 100 mg tablets, as 10 mg/ml oral solution and as 50 mg/5 ml single-dose vial injection, for intravenous use.

SUMMARY OF THE INVENTION

In one embodiment, the present invention provides a process for the preparation of brivaracetam, a compound of formula I, or a salt thereof,

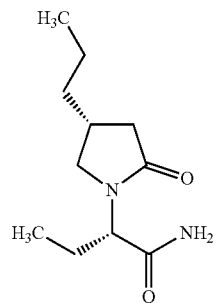

the process comprising:

i) reacting a compound of formula VI with L-menthol to obtain a compound of formula IV,

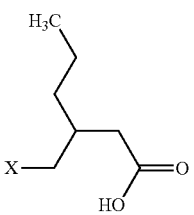

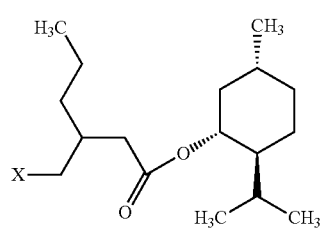

wherein X=Cl, Br, I, OMs or OTs;

ii) reacting the compound of formula IV with (2S)-2-aminobutanamide, a compound of formula III, to obtain a diastereomeric mixture, a compound of formula II;

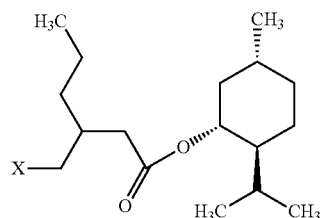

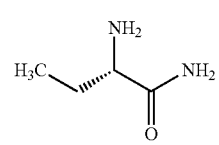

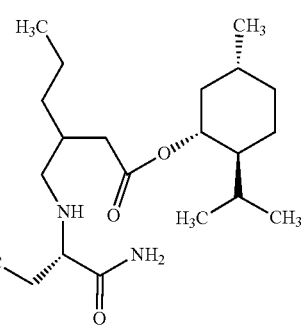

iii) separating the desired diastereomer, a compound of formula IIA and the undesired diastereomer, a compound of formula IIB, from the diastereomeric mixture, the compound of formula II; and

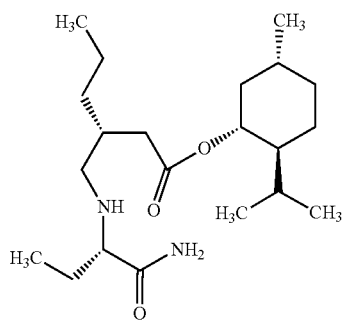
IIA

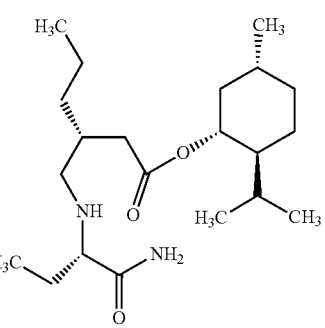
IIA wherein X=Cl, Br, I, OMs or OTs.

In one embodiment, the present invention provides a process for the preparation of brivaracetam, a compound of formula I, or salt thereof,

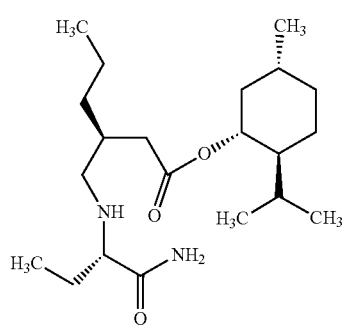
IIB

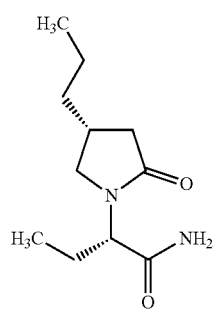
I iv) cyclizing the compound of formula IIA, to obtain brivaracetam, the compound of formula I.

In one embodiment, the present invention provides a compound of formula II, IIA and a compound of formula IV, comprising the steps of:

i) reacting the compound of formula IV with (2S)-2-aminobutanamide, a compound of formula III, to obtain a diastereomeric mixture, a compound of formula II; and

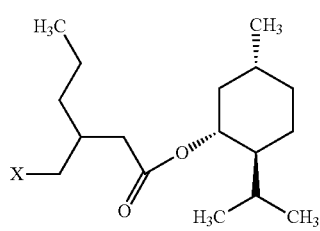
IV

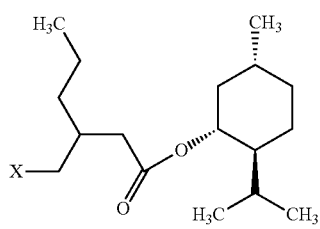
IV

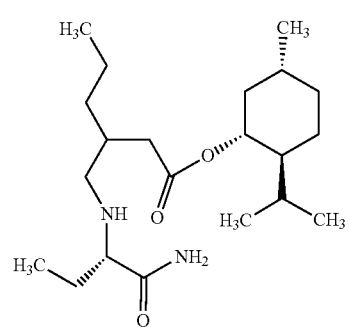
II

III $H_3C$ $NH_2$ $NH_2$ $O$

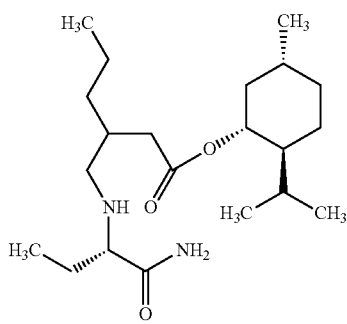
II ii) separating the desired diastereomer, a compound of formula IIA and the undesired diastereomer, a compound of formula IIB, from the diastereomeric mixture, the compound of formula II.

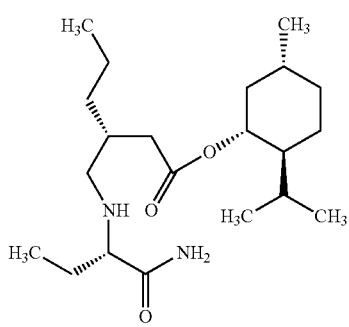
IIA

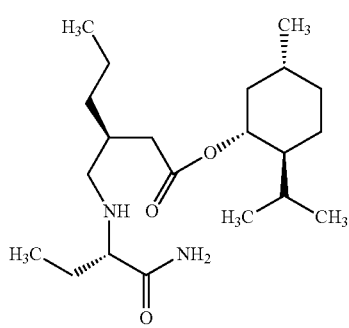
IIB

In one embodiment, the present invention provides use of compound of formula II, IIA and IV in the preparation of brivaracetam, the compound of formula I,

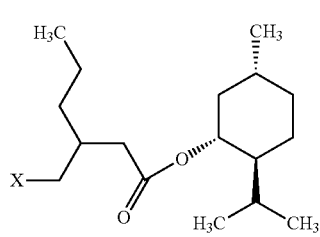
IV

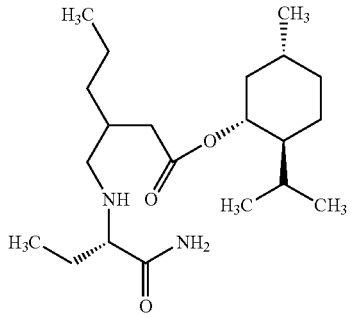
II

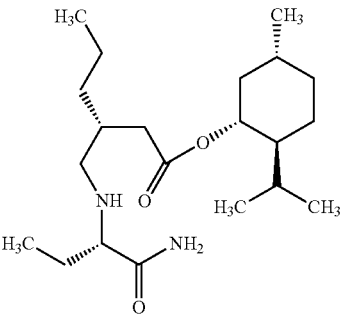
IIA wherein X=Cl, Br, I, OMs, or OTs.

In one embodiment, the present invention provides a process for the preparation of brivaracetam, a compound of formula I, or a salt thereof,

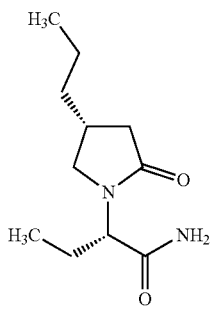
I the process comprising:
(a) obtaining a diastereomeric mixture, a compound of formula II,

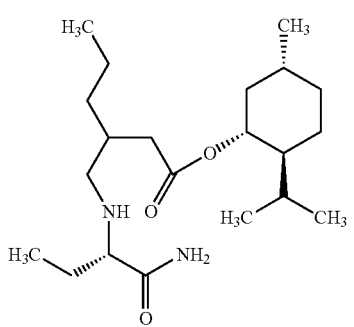
II by any one of the following:
(i) reacting the compound of formula IV wherein X=Cl, Br, I, OMs or OTs, with (2S)-2-aminobutanamide, a compound of formula III,

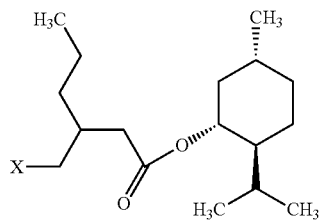

or
(ii) reacting a compound of formula VIII with L-menthol,

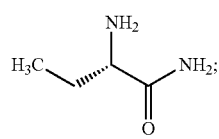

or
(iii) reacting a compound of formula IX with L-menthol,

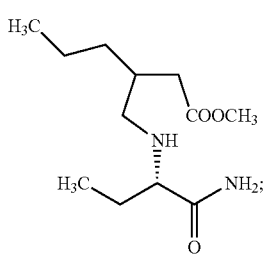

or
(iv) reducing a compound of formula X,

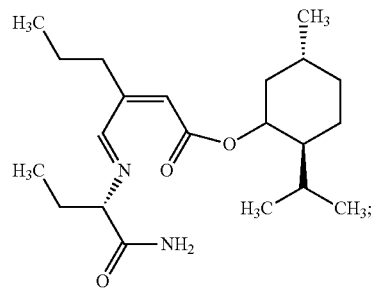

(b) separating the desired diastereomer, a compound of formula IIA and the undesired diastereomer, a compound of formula IIB, from the diastereomeric mixture, the compound of formula II; and

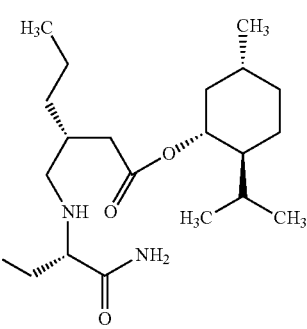

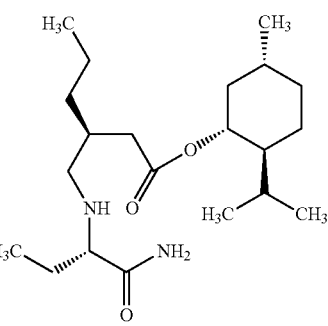

c) cyclizing the compound of formula IIA, to obtain brivaracetam the compound of formula I.

DETAILED DESCRIPTION OF THE INVENTION

In one embodiment, the present invention provides a process for the preparation of brivaracetam, a compound of formula I, or a salt thereof,

9

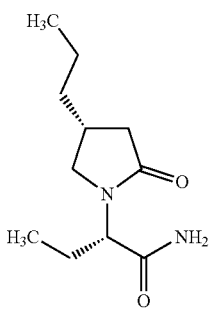
I the process comprising:
  i) reacting a compound of formula VI with L-menthol to obtain a compound of formula IV,

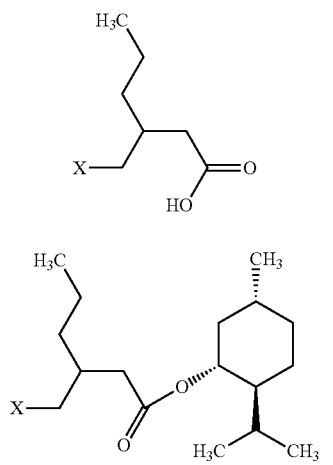
VI

IV wherein X=Cl, Br, I, OMs or OTs;
  ii) reacting the compound of formula IV with (2S)-2-aminobutanamide, a compound of formula III, to obtain a diastereomeric mixture, a compound of formula II;

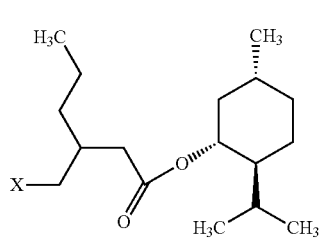
IV

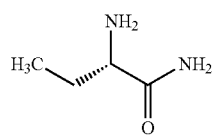
III

10
-continued

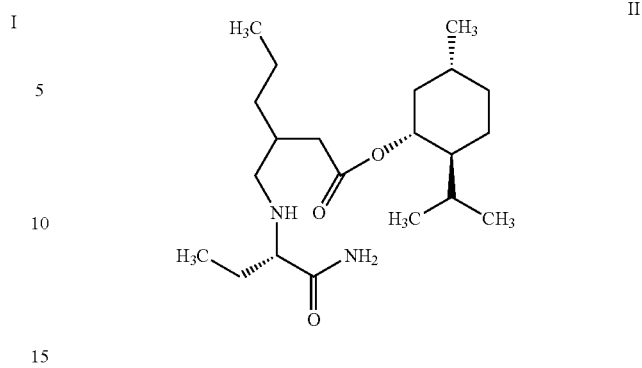
II iii) separating the desired diastereomer, a compound of formula IIA and the undesired diastereomer, a compound of formula IIB, from the diastereomeric mixture, the compound of formula II; and

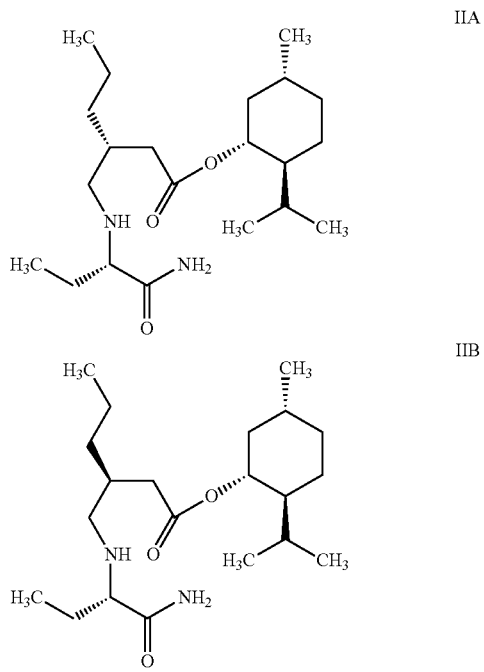
IIA

IIB iv) cyclizing the compound of formula IIA, to obtain brivaracetam the compound of formula I.

In step 'i' of the above process, the compound of formula VI is reacted with L-menthol in the presence of a coupling reagent.

In one embodiment, the coupling reagent may be selected from the group consisting of thionyl chloride, carbodiimides, 1-hydroxybenzotriazole based or 1-hydroxy-7-azabenzotriazole based phosphonium and uronium salts, sulfinyl halide, phosphorus halide, oxalyl chloride, and the like.

In one embodiment, the carbodiimide coupling reagent may be selected from the group consisting of N,N'-dialkylcarbodiimides such as N,N'-dicyclohexylcarbodiimide (DCC) or diisopropylcarbodiimide (DIPC), 1-ethyl-3-(3-dimethylaminopropyl)-carbodiimide (EDC) and the like.

In one embodiment, 1-hydroxybenzotriazole and 1-hydroxy-7-azabenzotriazole based phosphonium salt may be selected from the group consisting of benzotriazol-1-yl-N-oxy-tris(dimethylamino)phosphoniumhexafluorophosphate (BOP), benzotriazol-1-yl-N-oxy-tris(pyrrolidino)phosphonium hexafluorophosphate (PyBOP), 7-azabenzotriazol-1-yl-N-oxy-tris(pyrrolidino)phosphonium hexafluoro phosphate (PyAOP) and the like.

In one embodiment, 1-hydroxybenzotriazole and 1-hydroxy-7-azabenzotriazole based uronium salt may be selected from the group consisting of N-[(lHbenzotriazol-1-yl)(dimethylamino)methylene]-N-methylmethan-aminium hexafluorophosphate N-oxide (HBTU) and the like.

In one embodiment, phosphorus halide may be selected from the group consisting of phosphorus oxychloride, phosphorus trichloride, phosphorus pentachloride and the like.

In one embodiment, the present invention provides a process wherein the reaction of the compound of formula VI with L-menthol in step 'i' may be carried out in the presence of coupling reagent, wherein the coupling reagent is thionyl chloride.

In one embodiment, the reaction of compound of formula VI with L-menthol, to obtain a compound of formula IV may be carried out in a solvent.

In one embodiment, the solvent may be selected from the group consisting of haloalkane such as methylene dichloride, chloroform, ethylene dichloride and the like; ether such as tetrahydrofuran, dioxane; amide such as dimethylformamide; hydrocarbon such as toluene, xylene and the like and mixtures thereof.

In one embodiment, the present invention provides a process wherein a compound of formula V,

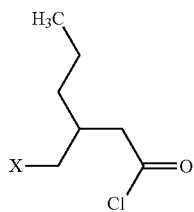

V wherein X=Cl, Br, I, OMs, or OTs, may be formed as an intermediate in the reaction of compound of formula VI with L-menthol, in the presence of coupling reagent, wherein the coupling reagent is thionyl chloride.

In one embodiment, the compound of formula V may be isolated or formed in situ.

In one embodiment, the present invention provides a process wherein a compound of formula VA,

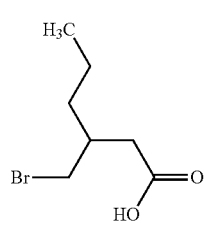

VIA

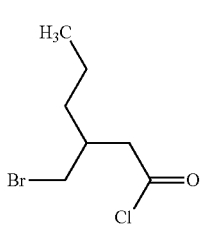

VA may be formed as an intermediate in the reaction of compound of formula VIA with L-menthol, in the presence of a coupling reagent, wherein the coupling reagent is thionyl chloride.

In step 'ii' of the above process, compound of formula IV may be reacted with (2S)-2-aminobutanamide, compound of formula III, to obtain a diastereomeric mixture a compound of formula II.

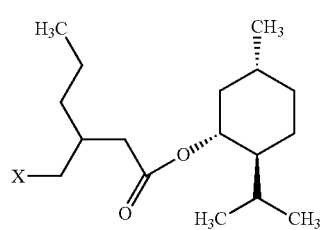

IV

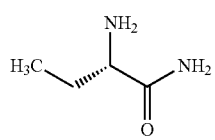

III

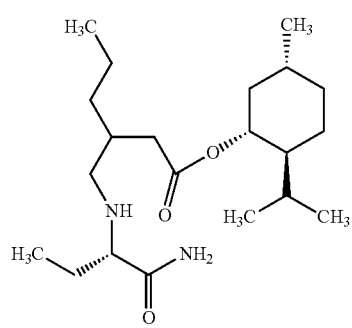

II

In one embodiment, the present invention provides a process, wherein the compound of formula IV may be reacted with (2S)-2-aminobutanamide, a compound of formula III, to obtain a diastereomeric mixture, a compound of formula II in the presence of a base.

In one embodiment, the base may be selected from the group consisting of alkali metal hydroxide like sodium hydroxide, potassium hydroxide, alkaline earth metal hydroxides like calcium hydroxide, alkoxides like sodium methoxide, sodium or potassium tert butoxide, alkali metal carbonate such as sodium carbonate, alkaline earth metal carbonates like calcium carbonates, sodium hydride, lithium bis(trimethylsilyl)amide and the like, and mixtures thereof.

In one embodiment, the reaction of the compound of formula IV with (2S)-2-aminobutanamide, the compound of formula III, may be carried out in presence of a phase transfer catalyst. In one embodiment, the phase transfer catalyst may be selected from the group consisting of quaternary ammonium salts like tetra butyl ammonium bromide (TBAB), tetrabutyl ammonium fluoride (TBAF), tetra butyl ammonium hydroxide (TBAH), tetrabutyl ammonium iodide (TBAI), crown ether, phosphonium salts, sodium iodide, potassium iodide, and the like; and mixtures thereof.

In one embodiment, the compound of formula IV may be reacted with (2S)-2-aminobutanamide, the compound of formula III, in a solvent.

In embodiment, the solvent may be selected from the group consisting of C1-C6 aliphatic ester such as ethyl acetate, isopropyl acetate, n-butyl acetate and the like; amide such as dimethyl formamide, dimethyl acetamide and the like; nitrile such as acetonitrile and the like; sulfoxide such dimethyl sulfoxide and the like and the mixture thereof.

In step 'iii' of the above process, the desired diastereomer, a compound of formula IIA and the undesired diastereomer, a compound of formula IIB, may be separated from the diastereomeric mixture, the compound of formula II.

In one embodiment, the present invention provides a process, wherein in step 'iii', the separation of desired diastereomer, the compound of formula IIA, and the undesired diastereomer, the compound of formula IIB, from the diastereomeric mixture, the compound of formula II, may be carried out by any of the following:
x) by treating diastereomeric mixture, the compound of formula II, with a solvent in which one of the diastereomer is soluble and other diastereomer is insoluble and precipitated out; or
y) by treating diastereomeric mixture, the compound of formula II, with a solvent and adding an anti-solvent to it in which one of the diastereomer is soluble and other diastereomer is insoluble and precipitated out.

In one embodiment, the separation of desired diastereomer, the compound of formula IIA, and the undesired diastereomer, the compound of formula IIB from the diastereomeric mixture, the compound of formula II, may be carried out by treatment with a solvent, in 'x', wherein one of the diastereomer is selectively precipitated based on the differential solubility of the diastereomers, IIA and IIB in the solvent.

In one embodiment, the treatment with solvent comprises subjecting the diastereomeric mixture, the compound of formula II to washing, slurrying, crystallizing with the solvent.

In one embodiment, the treatment with solvent comprises subjecting the diastereomeric mixture, the compound of formula II to washing, slurrying, crystallizing with the solvent at a temperature in the range of 0° C. to about 100° C.

In one embodiment, the desired diastereomer, the compound of formula IIA may be selectively separated from the undesired diastereomer, the compound of formula IIB, by being insoluble and precipitated in the solvent, and the undesired diastereomer, the compound of formula IIB, being soluble in the solvent.

In one embodiment, the solvent used in 'x' may be selected from the group consisting of C1-C6 aliphatic ester and C1-6 aliphatic ketone.

In one embodiment, C1-C6 aliphatic ester may be selected from the group consisting of ethyl acetate, propyl acetate, isopropyl acetate, butyl acetate, isobutyl acetate, and t-butyl acetate and the like.

In one embodiment, C1-C6 ketone may be selected from the group consisting of acetone, ethyl methyl ketone and methyl isobutyl ketone and the like.

In one embodiment, the desired diastereomer, the compound of formula IIA may be selectively separated from the undesired diastereomer, the compound of formula IIB, by being insoluble and precipitated in isopropyl acetate, and the undesired diastereomer, the compound of formula IIB, being soluble in isopropyl acetate.

In one embodiment, the desired diastereomer, the compound of formula IIA may be selectively separated from the undesired diastereomer, the compound of formula IIB, by being insoluble and precipitated in acetone, and the undesired diastereomer, the compound of formula IIB, being soluble in acetone.

In one embodiment, the diastereomeric mixture, the compound of formula II may be treated with a solvent, in 'x', wherein the desired diastereomer, the compound of formula IIA, is soluble and undesired diastereomer, the compound of formula IIB, is insoluble and precipitated out.

In one embodiment, the diastereomeric mixture, the compound of formula II, may be treated with a solvent at the temperature of about 0° C. to about 100° C. In one embodiment, the diastereomeric mixture, the compound of formula II, may be treated with a solvent at the temperature of about 0° C. to about 80° C. In one embodiment, the diastereomeric mixture, the compound of formula II, may be treated with a solvent at the temperature of about 20° C. to about 100° C. In one embodiment, the diastereomeric mixture, the compound of formula II, may be treated with a solvent at the temperature of about 20° C. to about 80° C.

In one embodiment, the diastereomeric mixture, the compound of formula II, may be treated with a solvent for about 1 h to about 12 h. In one embodiment, the diastereomeric mixture, the compound of formula II, may be treated with a solvent for about 2 h to about 8 h. In one embodiment, the diastereomeric mixture, the compound of formula II, may be treated with a solvent for about 2 h to about 6 h. In one embodiment, the diastereomeric mixture, the compound of formula II, may be treated with a solvent for about 1 h to about 2 h.

In one embodiment, the desired diastereomer, the compound of formula IIA is selectively separated from the undesired diastereomer, the compound of formula IIB, by treatment of diastereomeric mixture, the compound of formula II, with a solvent, wherein treatment with a solvent may involve slurrying in a solvent, recrystallization.

In one embodiment, the slurrying of diastereomeric mixture, the compound of formula II, in a solvent may be carried out at the temperature of about 0° C. to about 100° C. In one embodiment, the slurrying of diastereomeric mixture, the compound of formula II, in a solvent may be carried out at the temperature of about 0° C. to about 80° C. In one embodiment, the slurrying of diastereomeric mixture, the compound of formula II, in a solvent may be carried out at the temperature of about 0° C. to about 40° C. In one embodiment, the slurrying of diastereomeric mixture, the compound of formula II, in a solvent may be carried out at the temperature of about 0° C. to about 5° C.

In one embodiment, the slurrying of diastereomeric mixture, the compound of formula II, in a solvent may be carried out for about 2 h to about 24 h. In one embodiment, the slurrying of diastereomeric mixture, the compound of formula II, in a solvent may be carried out for about 12 to about 24 h. In one embodiment, the slurrying of diastereomeric mixture, the compound of formula II, in a solvent may be carried out for about 6 h to about 12 h.

In one embodiment, the desired diastereomer, the compound of formula IIA may be selectively separated from the undesired diastereomer, the compound of formula IIB by recrystallizing the diastereomeric mixture, the compound of formula II.

In one embodiment, the recrystallization may be carried out by heating the diastereomeric mixture, the compound of formula II in a solvent at about 40° C. to about 100° C. and subsequently cooling to about 0° C. to about 30° C., wherein the desired diastereomer, the compound of formula IIA, precipitate out.

In one embodiment, the desired diastereomer, the compound of formula IIA, is separated from the undesired diastereomer, the compound of formula IIB, by dissolving the diastereomeric mixture, the compound of formula II, in a solvent and by addition of suitable anti-solvent wherein, one of the diastereomer is precipitated out.

In one embodiment, the desired diastereomer, the compound of formula IIA, is selectively separated from the undesired diastereomer, the compound of formula IIB, by dissolving the diastereomeric mixture, the compound of formula II, in a solvent and by addition of a suitable anti-solvent, wherein the desired diastereomer is insoluble and precipitated out.

In one embodiment, the solvent may be selected from the group consisting of C1-C6 alcohol such as methanol, ethanol, isopropyl alcohol and the like; haloalkane such as methylene dichloride, chloroform, ethylene dichloride and the like; ethers such as tetrahydrofuran and the like and mixtures thereof. In one embodiment, the anti-solvent may be selected from the group consisting of C1-C6 aliphatic ester such as ethyl acetate, isopropyl acetate, n-butyl acetate and the like; hydrocarbon such as n-heptane, cyclohexane and the like; nitrile such as acetonitrile and the like; and the mixtures thereof.

In one embodiment, the undesired diastereomer, the compound of formula IIB which is soluble in a solvent, is recycled.

In one embodiment, the undesired diastereomer, the compound of formula IIB, is recycled to generate the diastereomeric mixture, the compound of formula II by stirring and/or heating the solution containing the compound of formula IIB.

In step 'iv' of the above process, the compound IIA is cyclized to obtain brivaracetam, the compound of formula I.

In one embodiment, if required, the compound of formula IIA may be purified several times.

In one embodiment, in step 'iv', the cyclization of the compound of formula IIA is carried out in presence of an acid.

In one embodiment the acid may be selected from the group consisting of inorganic acid, organic acid and mixture thereof.

In one embodiment the inorganic acid may be selected from hydrochloric acid, sulphuric acid and the like. In one embodiment, the organic acid may be selected from the group consisting of acetic acid, trifluoroacetic acid, formic acid and the like.

In one embodiment, in step 'iv', the cyclization of the compound of formula IIA is carried out in presence of a base.

In one embodiment, the base may be selected from an organic or an inorganic base.

In one embodiment, the organic base may be selected from the group consisting of amines, organolithiums, tetraalkylammonium hydroxides, The amine may be selected from the group consisting of cyclic aliphatic amine, trialkyl amines, heterocyclic amine, C1-C6 aliphatic amine, C6-C12 aryl alkyl amines, C6-C12 aryl amines and the like. The cyclic aliphatic amine may be selected from the group consisting of cyclohexyl amine, dicyclohexyl amine, piperidine, piperazine and the like. The trialkyl amine may be selected from the group consisting of triethylamine, diisopropylethylamine (DIPEA) and the like. The heterocyclic amine may be selected from the group consisting of 1,8-diazabicyclo[5.4.0]undec-7-ene (DBU), 1,5-diazabicyclo[4.3.0]non-5-ene (DBN), 1,4-diazabicyclo[2.2.2]octane (Dabco) pyridine, pyrimidine, 4-(dimethylamino)pyridine (DMAP) and the like. The C1-C6 aliphatic amine may be selected from the group consisting of methyl amine, propyl amine, n-butylamine and the like. The C6-C12 aryl alkylamine may be selected from the group consisting of benzyl amine, phenyl ethyl amine, and the like. The C6-C12 aryl amine may be selected from the group consisting of aniline and the like. The organolithium may be selected from the group consisting of methyllithium, n-butyllithium, t-butyllithium and the like.

In one embodiment the inorganic base may be selected from the group consisting of metal carbonate, metal bicarbonate, metal hydroxide and metal alkoxides wherein the metal may be selected from the group consisting of sodium, potassium, lithium, calcium, cesium or magnesium. The metal carbonate may be selected from the group consisting of sodium carbonate, potassium carbonate, lithium carbonate, calcium carbonate, cesium carbonate, magnesium carbonate and the like. The metal bicarbonate may be selected from the group consisting of sodium bicarbonate, potassium bicarbonate, lithium bicarbonate, calcium bicarbonate, cesium bicarbonate, magnesium bicarbonate and the like. The metal hydroxide may be selected from the group consisting of sodium hydroxide, potassium hydroxide, lithium hydroxide, calcium hydroxide, cesium hydroxide, magnesium hydroxide and the like. The metal alkoxide may be selected from the group consisting of sodium methoxide, potassium t-butoxide, sodium ethoxide and the like.

In one embodiment, the present invention provides a process wherein the compound of formula VI is prepared by ring opening of a compound of formula VII.

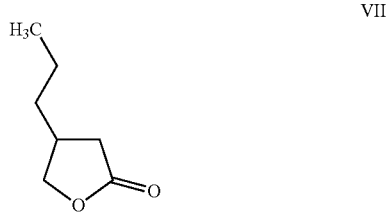

VII

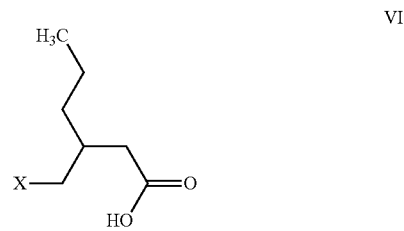

VI

In one embodiment, the ring opening of the compound of formula VII may be carried out by reacting it with hydrogen halide in presence of an acid.

In one embodiment, the present invention provides a compound of formula IV,

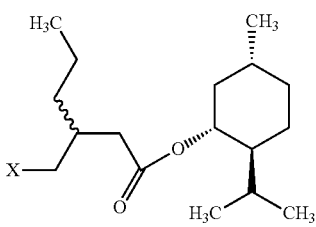

wherein X=Cl, Br, I, OMs, or OTs.

In one embodiment, the present invention provides a compound of formula IV, wherein X is Br.

In one embodiment, the present invention provides a compound of formula IV, wherein X is Br, characterized with 1H NMR having characteristics peaks at δ: 4.74-4.67 (m, 1H), 3.57-3.47 (m, 2H), 2.51-2.50 (d, 1H), 2.49-2.44 (dd, 1H), 2.36-2.35 (d, 1H), 2.32-2.31 (d, 1H), 2.20-1.87 (m, 1H), 1.71-1.66 (m, 2H), 1.50-1.27 (m, 6H), 1.08-0.86 (m, 12H), 0.78-0.76 (d, 3H).

In one embodiment, the present invention provides a compound of formula II,

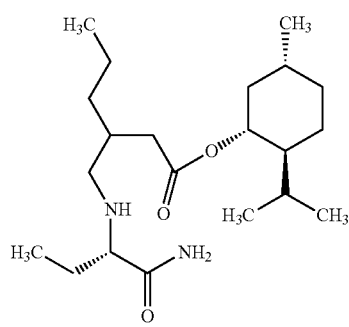

In one embodiment, the present invention provides (1R, 2S,5R)-5-methyl-2-(propan-2-yl)cyclohexyl 3-({[(2S)-1-amino-1-oxobutan-2-yl]amino}methyl) hexanoate, the compound of formula II.

In one embodiment, the present invention provides a compound of formula IIA,

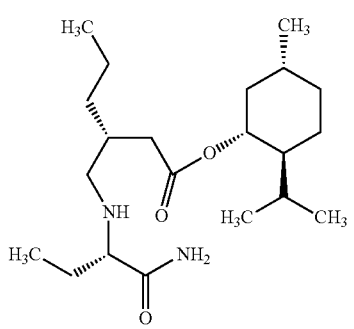

In one embodiment, the present invention provides (1R, 2S,5R)-5-methyl-2-(propan-2-yl)cyclohexyl (3R)-3-({[(2S)-1-amino-1-oxobutan-2-yl]amino}methyl) hexanoate, the compound of formula IIA.

In one embodiment, the present invention provides a compound of formula IIA, characterized with 1H NMR having characteristics peaks at δ: 7.08, 5.46, 4.73-4.66, 3.40-3.36, 2.58-2.53, 2.34-2.31, 2.02-1.96, 1.87-1.75, 1.70-1.30, 1.28-0.9, 0.7.

In one embodiment, the present invention provides a crystalline compound of formula IIA.

In one embodiment, the present invention provides a compound of formula IIA, wherein the content of the compound of formula IIB, is less than 1% with respect to compound of formula IIA, as determined by HPLC.

In one embodiment, the present invention provides a process for the preparation of brivaracetam, a compound of formula I, or salt thereof, comprising the steps of:

i) reacting the compound of formula IV with (2S)-2-aminobutanamide, a compound of formula III, to obtain a diastereomeric mixture, a compound of formula II; and ii) separating the desired diastereomer, a compound of formula IIA and the undesired diastereomer, a compound of formula IIB, from the diastereomeric mixture, the compound of formula II.

In one embodiment, the process used is as discussed supra.

In one embodiment, present invention provides a process wherein brivaracetam, the compound of formula I, is obtained in a diastereomeric excess of at least 98%, as determined by HPLC.

In one embodiment, the present invention provides use of the compound of formula II, IIA and IV, in the preparation of brivaracetam, the compound of formula I.

In one embodiment, the present invention provides a process wherein (2S)-2-[(4R)-2-oxo-4-propylpyrrolidin-1-yl]butanamide, brivaracetam, the compound of formula I, is obtained in a chemical purity of at least 99% and wherein the level of one or more compounds of formula A, B, C or IIA is less than 0.15% w/w relative to the amount of brivaracetam as determined by HPLC,

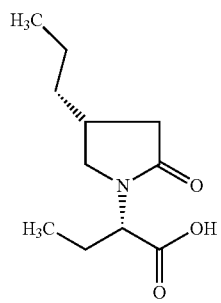

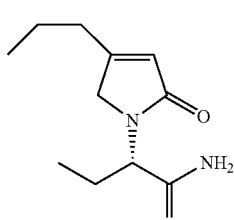

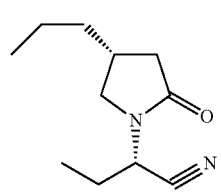

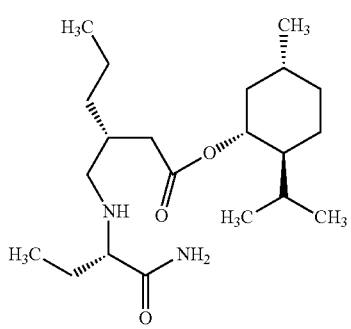

IIA

In one embodiment, the present invention provides (2S)-2-[(4R)-2-oxo-4-propylpyrrolidin-1-yl]butanamide, brivaracetam, the compound of formula I, wherein the content of (2S,4S) and/or (2R,4S) and/or (2R,4R) isomers of the compound of formula I, is less than 1% w/w with respect to (2S)-2-[(4R)-2-oxo-4-propylpyrrolidin-1-yl]butanamide, the compound of formula I, as determined by HPLC.

The present invention provides brivaracetam obtained by above process, as analyzed by chemical purity using high performance liquid chromatography (HPLC) with the conditions described below:

Method-I:
Chromatographic Conditions:
  Apparatus: A High Performance Liquid Chromatograph equipped with quaternary gradient pumps, variable wavelength UV detector attached with data recorder and integrator software.
  Column: Zorbax Eclipse plus C8, 150×4.6 mm, 3.5μ; Column temperature: 50° C.
  Sample Cooler temperature: 10° C.
  Mobile Phase A: Water:Acetonitrile:Ortho-phosphoric acid (90:10:0.1) v/v/v.
  Mobile Phase B: Water:Acetonitrile:Ortho-phosphoric acid (10:90:0.1) v/v/v.

| Time (min.) | % Mobile Phase A | % Mobile Phase B |
|---|---|---|
| 0.01 | 95 | 05 |
| 18.0 | 72 | 28 |
| 35.0 | 55 | 45 |
| 45.0 | 30 | 70 |
| 54.0 | 30 | 70 |
| 55.0 | 95 | 05 |
| 60.0 | 95 | 05 |

Diluent: Water:Acetonitrile (80:20, v/v); Flow Rate: 1.0 mL/minute; Detection: UV 215 nm; Injection Volume: 50 μL; Run time: 60 minutes The retention time of brivaracetam is about 11.7 minutes under these conditions. Relative retention time for compound of formula A is about 1.37, compound of formula B is about 0.83 and compound of formula C is about 1.86 with respect to brivaracetam.

Method-II:
Chromatographic Conditions:
  Apparatus: A High Performance Liquid Chromatograph equipped with quaternary gradient pumps, variable wavelength UV detector attached with data recorder and integrator software.
  Column: YMC triart, C8, 150×4.6 mm, 3μ; Column temperature: 40° C.
  Sample Cooler temperature: 10° C.
  Mobile Phase A: Buffer:Acetonitrile (95:05, v/v); Buffer: 0.01M Disodium hydrogen phosphate in water adjust the pH to 8.00 with 10% v/v Orthophosphoric acid in water
  Mobile Phase B: Acetonitrile

| Time (min.) | % Mobile Phase A | % Mobile Phase B |
|---|---|---|
| 0.01 | 70 | 30 |
| 30 | 30 | 70 |
| 35 | 30 | 70 |
| 38 | 70 | 30 |
| 45 | 70 | 30 |

Diluent: Methanol:Water (95:05, v/v); Flow Rate: 1.0 mL/minute; Detection: UV 215 nm; Injection Volume: 40 μL; Run time: 45 minutes The retention time of compound of formula IIA is about 26.0 minutes under these conditions.

Method-III:
Chromatographic Conditions:
  Apparatus: A High Performance Liquid Chromatograph equipped with quaternary gradient pumps, variable wavelength UV detector attached with data recorder and integrator software.
  Column: Chiralpak AD-H, 250×4.6 mm, 5μ; Column temperature: 30° C.
  Sample cooler temperature: 25° C.
  Mobile Phase: n-Hexane:Isopropyl alcohol:Trifluroacetic acid:Diethylamine (930:70:1:1, v/v/v/v)
  Diluent: n-Hexane:Isopropyl alcohol (80:20, v/v); Flow Rate: 1.0 mL/minute;
  Detection: UV 215 nm; Injection Volume: 30 μL; Run time: 50 minutes The retention time of brivaracetam is about 27.0 minutes under these conditions. Relative retention time for (2S,4S), (2R,4S) and (2R,4R) isomer of the compound of formula I is about 0.73, 0.43 and 0.47 respectively with respect to brivaracetam.

In one embodiment, the present invention provides a process for the preparation of brivaracetam, a compound of formula I, or a salt thereof, the process comprising:
  i) reacting a compound of formula VI with chiral alcohol R—OH to obtain a compound of formula IV" in presence of a coupling reagent,

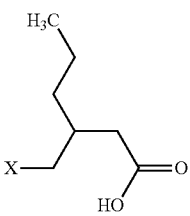

VI

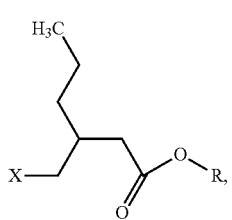

IV"

wherein X=Cl, Br, I, OMs, or OTs;

ii) reacting the compound of formula IV″ with (2S)-2-aminobutanamide, a compound of formula III, to obtain a diastereomeric mixture, a compound of formula II″;

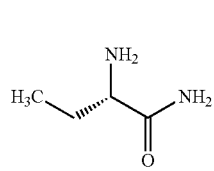

III

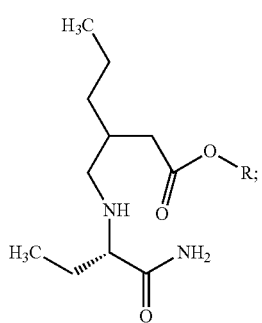

II″ iii) separating the desired diastereomer, a compound of formula II″A and the undesired diastereomer, a compound of formula II″B, from the diastereomeric mixture, the compound of formula II″; and

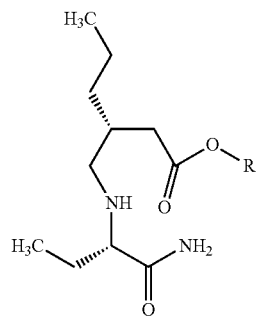

II″A

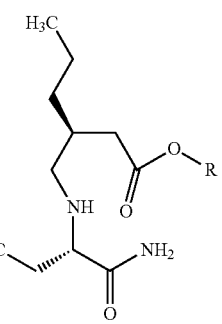

II″B iv) cyclizing the compound of formula II″A, to obtain brivaracetam the compound of formula I.

In one embodiment, the chiral alcohol R—OH, R may be selected from the group consisting of L-menthol, D-menthol, (+)-neomenthol, (1R)-(−)-nopol, 2-methylisoborneol and menthol derivatives.

In one embodiment, the present invention provides a process for the preparation of compound of formula IIA as depicted in scheme 1.

Scheme 1

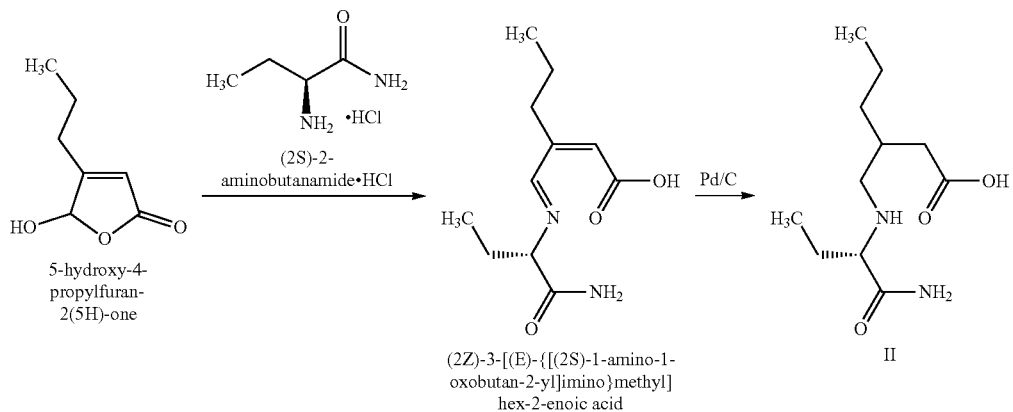

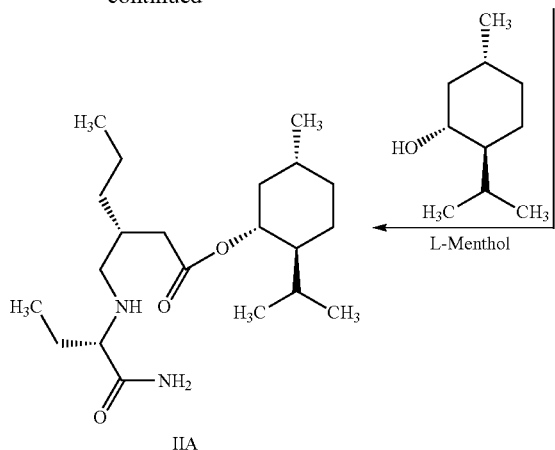
In one embodiment, the present invention provides a process for the preparation of compound of formula IIA as depicted in scheme 2.
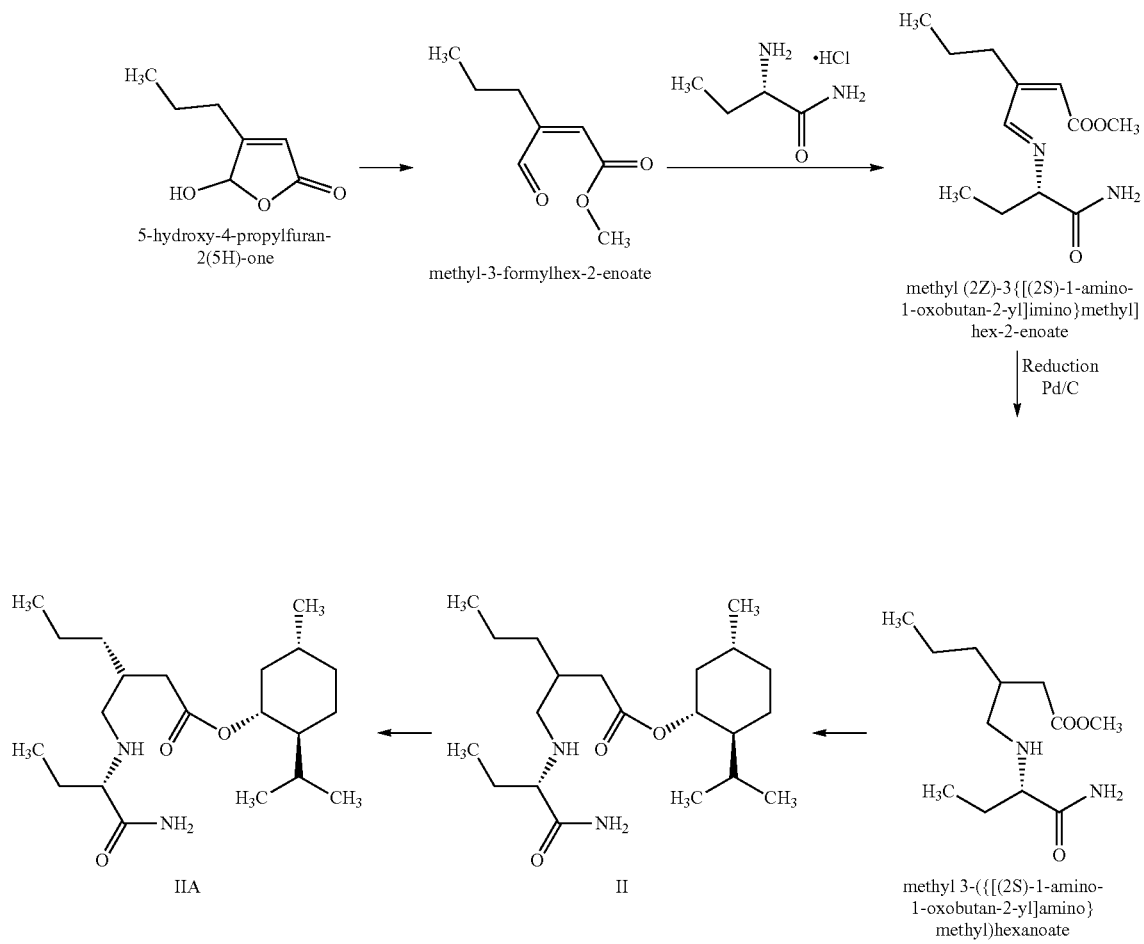
In one embodiment, the present invention provides a process for the preparation of compound of formula IIA as depicted in scheme 3.

Scheme 3
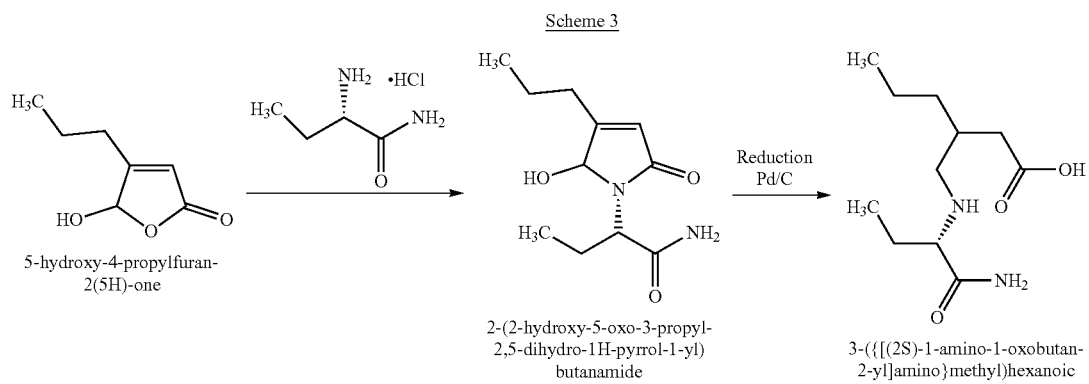
In one embodiment, the present invention provides a process for the preparation of compound of formula IIA as depicted in scheme 4.
Scheme 4
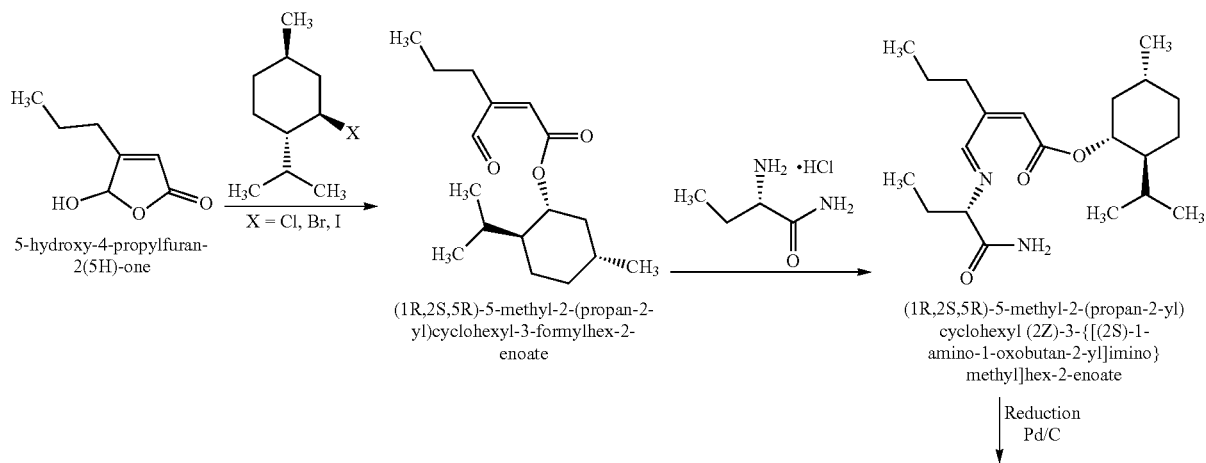

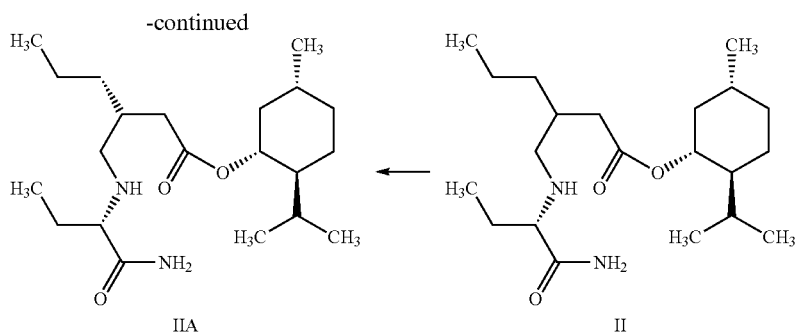

In one embodiment, the present invention provides a process for the preparation of brivaracetam, a compound of formula I, or a salt thereof,

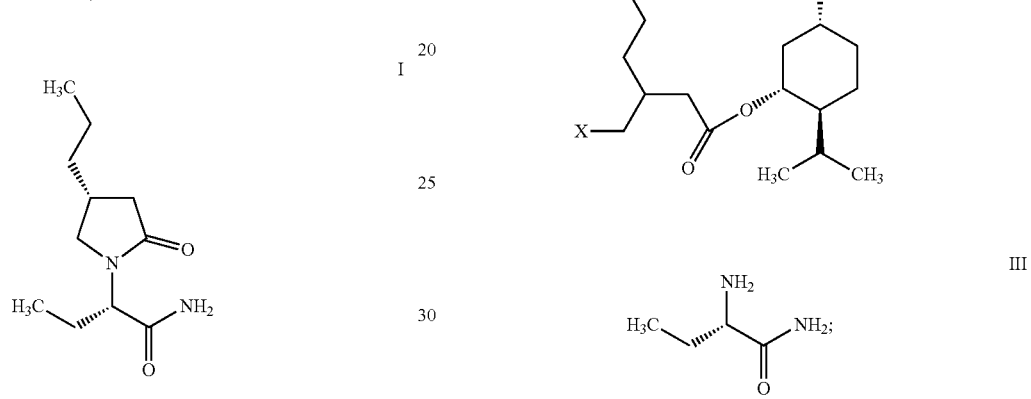

the process comprising:
(a) obtaining a diastereomeric mixture, a compound of formula II, by any one of the following:
(i) reacting the compound of formula IV wherein X=Cl, Br, I, OMs or OTs, with (2S)-2-aminobutanamide, a compound of formula III, or
(ii) reacting a compound of formula VIII with L-menthol, or
(iii) reacting a compound of formula IX with L-menthol,

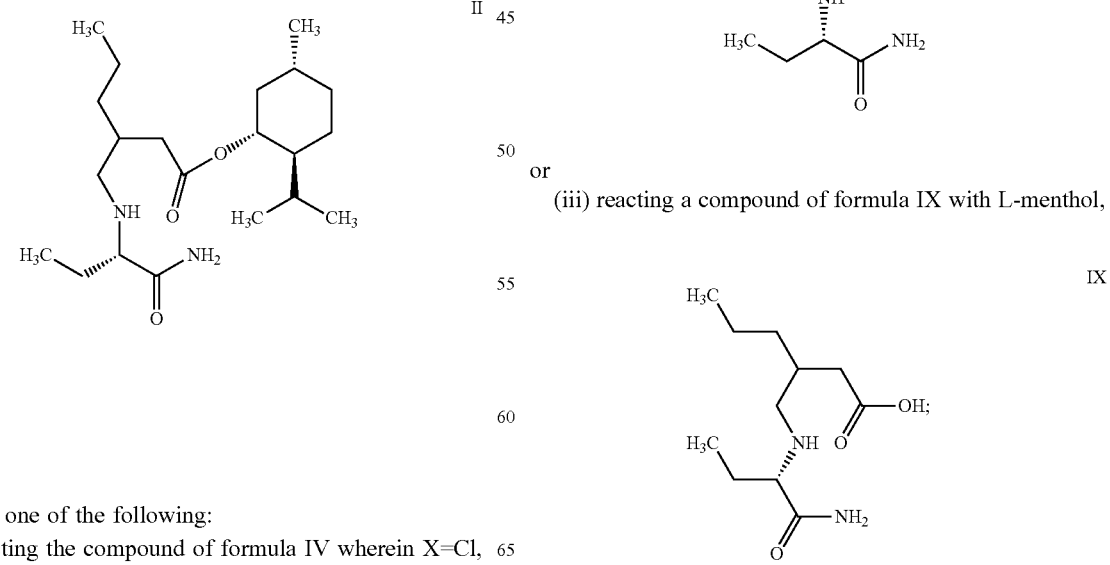

or (iv) reducing a compound of formula X,

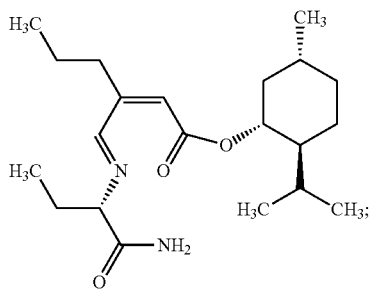

(b) separating the desired diastereomer, a compound of formula IIA and the undesired diastereomer, a compound of formula IIB, from the diastereomeric mixture, the compound of formula II; and

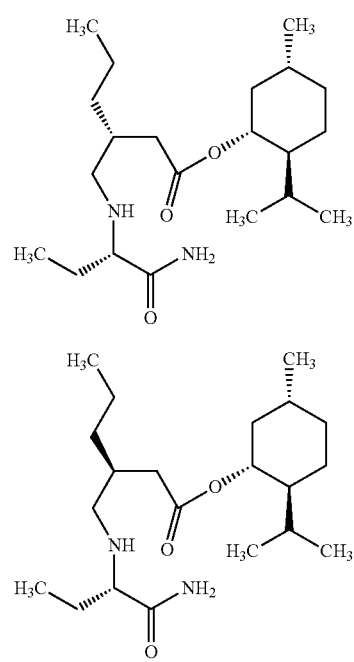

c) cyclizing the compound of formula IIA, to obtain brivaracetam the compound of formula I.

The process step (ai) is as discussed supra.

In one embodiment, the process step (aii) is carried out by reacting the compound of formula VIII with L-menthol in presence of a catalyst.

In one embodiment, the catalyst selected is DMAP.

In one embodiment, the reaction is carried out by azeotropically.

In one embodiment, the process step (aiii) is carried out by reacting the compound of formula IX with L-menthol in presence of a coupling reagent.

In one embodiment, the coupling reagent is selected from the group consisting of thionyl chloride, carbodiimides, 1-hydroxybenzotriazole based or 1-hydroxy-7-azabenzotriazole based phosphonium and uronium salts, sulfinyl halide and phosphorus halide.

In one embodiment, the process step (aiv) is carried out by reducing a compound of formula X using hydrogen source in the presence a metal catalyst.

In one embodiment, the hydrogen source is selected from the group consisting of hydrogen gas, formic acid, isopropanol, and dihydroanthracene.

In one embodiment, the metal catalyst is selected from the group consisting of nickel, palladium, platinum, ruthenium, rhodium and iridium.

The process steps (b) and (c) are as discussed supra.

The examples that follow are provided to enable one skilled in the art to practice the invention and are merely illustrative of the invention. The examples should not be read as limiting the scope of the invention as defined in the features and advantages.

EXAMPLES

Example 1: Preparation of 5-hydroxy-4-propylfuran-2(5H)-one

Morpholine (256.5 g) was added to n-heptane (800 ml) and cooled to about 0° C. to about 5° C. Glyoxylic acid was added to the reaction mass by maintaining the temperature between 0° C. to about 10° C. The reaction mixture was stirred for about 2 h to about 3 h at about 25° C. to about 30° C. N-Valeraldehyde (246.6 g) was added to the reaction mass at about 25° C. to about 30° C. The temperature of reaction mass slowly raised to 40-45° C. and stirred for about 18 h to about 24 h. After the completion of reaction, the reaction mass was cooled to about 25° C. to about 30° C., quenched with conc. hydrochloric acid (500 ml) and stirred for about 2 h to about 3 h at about 25° C. to about 30° C. The layers were separated and aqueous layer was washed with n-heptane (400 ml). To the residue, ethyl acetate (800 ml) was added under stirring; sodium carbonate (84 g) was added by controlling frothing and stirred for about 20 min to about 30 min. The layers were separated and aqueous layer was extracted with ethyl acetate, washed with 20.0% sodium chloride solution. The organic layer thus obtained was distilled out under reduced pressure and degassed to obtain 5-hydroxy-4-propylfuran-2(5H)-one as oily mass (Yield: 375 g).

Example 2: Preparation of 4-propylfuran-2(5H)-one 5-hydroxy-4-propylfuran-2(5H)-one (365 g) was added to ethanol (1825 ml) and cooled to about 0° C. to about 5° C. under inert atmosphere. Sodium borohydride (106.8 g) was added in lots by maintaining temperature below 10° C. The reaction mass stirred for about 1 h to about 2 h. After the completion of reaction, the reaction mass was quenched with acetic acid (169.5 g). The temperature of mass then raised to 40° C., distilled out under vacuum to obtain an oily mass. To this reaction mass water (1825 ml), conc. hydrochloric acid (274 ml) was added and stirred for about 2 h to about 3 h. To this, ethyl acetate (1825 ml) was added, stirred and the layer were separated. The aqueous layer was extracted with ethyl acetate, washed with 5.0% sodium chloride solution. The organic layer thus obtained was distilled out under reduced pressure and degassed to get title 4-propylfuran-2(5H)-one as an oily mass (263 g).

Example 3: Preparation of (R,S)-dihydro-4-propyl-furan-2(3H)-one (VII)

4-propylfuran-2(5H)-one (260 g) dissolved in Methanol (1820 mL) and transferred to hydrogenator. To the reaction mass 10%, 50.0% wet Pd/C (13 g) was added and stirred under hydrogen gas pressure (2-3 Kg) for about 2 h to about 3 h. After the completion of reaction, the reaction mass was filtered through hyflo bed and washed with methanol. The filtrate was distilled out under reduced pressure to obtain oily mass (250 g). The oily mass was distilled out under high vacuum to obtain compound VII (190 g).

Example 4: Preparation of 3-(bromomethyl)hexanoic (VI)

Hydrobromic acid in acetic acid (30-33%, 600 ml) was added to (R,S)-dihydro-4-propylfuran-2(3H)-one (200 g) at about 25° C. to about 30° C. under stirring. The reaction mixture was heated to about 50° C. to about 55° C. for about 2 h to about 3 h. After the completion of reaction, methylene dichloride (600 ml), water (400 ml) was added to the reaction mixture, stirred and layers were separated. The aqueous layer was extracted with methylene dichloride. The organic layer was washed with water, dried over anhydrous sodium sulphate and filtered to obtain solution of (R,S)-3-(bromomethyl)hexanoic acid compound VI.

Example 5: Preparation of (1R,2S,5R)-5-methyl-2-(propan-2-yl)cyclohexyl 2-(bromomethyl)hexanoate (IV)

Dimethylformamide (1.0 g) was added to the methylene dichloride solution of compound VI from Ex-1 and stirred. Thionyl chloride (371.34 g) was slowly added to the reaction mixture at about 20° C. to about 25° C. After the completion of reaction, the solvent was distilled out under reduced pressure to obtain (R,S)-3-(bromomethyl)hexanoyl chloride (compound V) as residue and was dissolved in methylene dichloride (200 ml). To this solution, L-Menthol (243.2 g) was added and stirred for about 2 h to about 3 h at the temperature of about 30° C. to about 35° C. After completion of reaction, methylene dichloride (600 ml), water (800 ml) was added to the reaction mixture, stirred and layers were separated. The organic layer was washed with water and aq sodium bicarbonate solution, dried over sodium sulphate and distilled out under reduced pressure to obtain (1R,2S,5R)-5-methyl-2-(propan-2-yl)cyclohexyl 3-(bromomethyl)hexanoate (compound IV) as oily mass which was dissolved in isopropyl acetate (2.5 ltr).

Example 6: Preparation of (1R,2S,5R)-5-methyl-2-(propan-2-yl)cyclohexyl 3-({[(2S)-1-amino-1-oxobutan-2-yl]amino]methyl)hexanoate (II)

To the solution of compound IV from Ex-2, (S)-2-aminobutanamide hydrochloride (323 g, compound III), tetrabutyl ammonium bromide (230 g) & anhydrous sodium carbonate (573 g) was added under stirring at about 20° C. to about 25° C. The suspension was then stirred for about 27 h to about 30 h at about 80° C. to about 85° C. After the completion of reaction, the reaction mass was cooled to about 25° C. to about 30° C., filtered to remove insolubles, washed Isopropyl acetate (200 ml). The filtrate was distilled out under reduced pressure and degassed to obtain the compound II as residue (yield: 550 g).

Example 7: Preparation of (1R,2S,5R)-5-methyl-2-(propan-2-yl)cyclohexyl (3R)-3-({[(2S)-1-amino-1-oxobutan-2-yl]amino]methyl)hexanoate (IIA)

To the residue obtained in Ex-3, isopropyl acetate was added, cooled to about 0° C. to about 5° C., stirred for about 2 h to about 3 h and filtered. The wet cake was washed with isopropyl acetate and dried at about 40° C. to about 45° C. under reduced pressure to obtain (1R,2S,5R)-5-methyl-2-(propan-2-yl)cyclohexyl (3R)-3-({[(2S)-1-amino-1-oxobutan-2-yl]amino}methyl)hexanoate (compound IIA, 179.0 g) as off white solids. HPLC purity >96%.

Example 8: Preparation of (1R,2S,5R)-5-methyl-2-(propan-2-yl)cyclohexyl (3R)-3-({[(2S)-1-amino-1-oxobutan-2-yl]amino]methyl)hexanoate (IIA)

The compound IIA (179 g) was added in isopropyl acetate (1790 ml) and stirred for about 2 h to about 4 h at about 80° C. to about 85° C. The reaction mass was cooled to about 25° C. to about 30° C. The precipitated solid was filtered and dried to obtain pure (1R,2S,5R)-5-methyl-2-(propan-2-yl)cyclohexyl(3R)-3-({[(2S)-1-amino-1-oxobutan-2-yl]amino}methyl)hexanoate (153 g); HPLC purity: 98% [α]D25=−48.54°, (c 1.0%, CHCl3). 1H NMR (400 MHz, CDCl3): δ 7.08 (b, 1H), 5.46 (b, 1H), 4.73-4.66 (m, 1H), 3.40-3.36 (m, 1H), 2.58-2.53 (m, 2H), 2.34-2.31 (m, 2H), 2.02-1.96 (m, 2H), 1.87-1.75 (m, 11H), 1.70-1.30 (m, 8H), 1.28-0.9 (m, 8H), 0.7 (m, 3H) Mass: M/Z=369 (M+H).

Example 9: Preparation of 1R,2S,5R)-5-methyl-2-(propan-2-yl)cyclohexyl 3-({[(2S)-1-amino-1-oxobutan-2-yl]amino]methyl)hexanoate (IIA)

The compound IIA (179 g) was added in isopropyl acetate (1790 ml) and stirred for about 2 h to about 4 h at about 80° C. to about 85° C. The reaction mass was cooled to about 0° C. to about 5° C. The precipitated solid was filtered and dried to obtain pure (1R,2S,5R)-5-methyl-2-(propan-2-yl)cyclohexyl(3R)-3-({[(2S)-1-amino-1-oxobutan-2-yl]amino}methyl)hexanoate (yield: 156 g), HPLC purity: >97%.

Example 10: Preparation of (2S)-2-[(4R)-2-oxo-4-propylpyrrolidin-1-yl]butanamide, Brivaracetam (I)

The compound IIA (100.0 g) was charged in a mixture of isopropyl acetate (1500.0 mL) and acetic acid (65.0 g), and stirred for about 4 h to about 5 h at about 85° C. to about 90° C. After the completion of reaction, the reaction mass was cooled to about 20° C. to about 30° C. and quenched in sodium chloride solution stirred for about 10 min to about 15 min and the layers were separated. To the organic layer, water and sodium bicarbonate (100 g) was slowly added and stirred for about 1 h to about 2 h. The layers were separated and organic layer was washed with sodium chloride solution, followed by distillation under reduced pressure to get oily mass. The oily mass was stirred in n-Heptane (700 ml) for about 10 h to about 12 h at about 25° C. to about 30° C. and filtered. The wet cake washed with n-heptane and dried to get crude brivaracetam (45 g). HPLC purity >99.50% and chiral purity 99.45%, 2S,4S isomer—0.50%, 2R,4S isomer—0.15%, 2R,4R isomer—0.15%.

Example 11: Preparation of (2S)-2-[(4R)-2-oxo-4-propylpyrrolidin-1-yl]butanamide, Brivaracetam (I)

Crude Brivaracetam (100.0 g) added to isopropyl acetate (200.0 mL) and stirred at about 50 to about 55° C., charcoalised and filtered through hyflo bed and washed with isopropyl acetate. The filtrate was heated to about 50° C. to about 55° C., n-heptane (1000.0 mL) was added slowly, and cooled gradually to 20° C. to about 25° C. and stirred for about 4 h to about 5 h and filtered. The wet cake was washed with mixture of isopropyl acetate (25 ml) and n-Heptane (50 ml) and dried. The obtained solid, diisopropyl ether (800.0 mL) was added and stirred at about 50° C. to about 55° C. The reaction mass was cooled gradually to about 0° C. to about 5° C., stirred, filtered and washed with chilled diisopropyl ether (80.0 mL). The solid was dried at about 50° C. to about 55° C. under reduced pressure to obtain brivaracetam (I). HPLC purity: >99.85%; Chiral purity: 99.85%, 2S,4S isomer: 0.15%

Example 12: Preparation of 3-(bromomethyl)hexanoic Acid (VI)

Hydrobromic acid in acetic acid (30-33%, 40 ml) was added to (R,S)-dihydro-4-propylfuran-2(3H)-one (10 g) at about 25° C. to about 30° C. under stirring. The reaction mixture was heated to about 50° C. to about 55° C. for about 2 h to about 3 h. Methylene dichloride, water was added to the reaction mixture and the two layers were separated. The aqueous layer was extracted with methylene dichloride. The combined organic layer was washed with water, dried over anhydrous sodium sulphate and filtered to obtain solution of (R,S)-3-(bromomethyl)hexanoic acid compound VI.

Example 13: Preparation of (1R,2S,5R)-5-methyl-2-(propan-2-yl)cyclohexyl 2-(bromomethyl)hexanoate (IV)

Dimethylformamide (0.025 g) was added to the methylene dichloride solution of compound VI obtained in Example 12. To the stirred reaction mixture was added thionyl chloride (18.6 g) at about 27° C. to about 32° C. After the completion of reaction, the solvent was distilled out under reduced pressure to obtain (R,S)-3-(bromomethyl) hexanoyl chloride (compound V) as residue and was dissolved in methylene dichloride (10 ml). To this solution, L-Menthol (12.2 g) was added and stirred for about 4 h to about 5 h at about 30° C. to about 35° C. After completion of reaction, water was added to the reaction mixture, stirred and layers were separated. The organic layer was washed with water and aqueous sodium bicarbonate solution, dried over sodium sulphate and distilled out under reduced pressure to obtain (1R,2S,5R)-5-methyl-2-(propan-2-yl)cyclohexyl 3-(bromomethyl)hexanoate (IV) as oily mass which was dissolved in isopropyl acetate (100 ml).

1H NMR (400 MHz, CDCl$_3$): δ 4.74-4.67 (m, 1H), 3.57-3.47 (m, 2H), 2.51-2.50 (d, 1H), 2.49-2.44 (dd, 1H), 2.36-2.35 (d, 1H), 2.32-2.31 (d, 1H), 2.20-1.87 (m, 1H), 1.71-1.66 (m, 2H), 1.50-1.27 (m, 6H), 1.08-0.86 (m, 12H), 0.78-0.76 (d, 3H)

Mass: M/Z=348.51 (M+H)

IR: 3439.31, 2949.21, 2874.82, 1724.89, 1416.23, 1096.68, 740.52 cm-1

Example 14: Preparation of (1R,2S,5R)-5-methyl-2-(propan-2-yl)cyclohexyl 3-({[(2S)-1-amino-1-oxobutan-2-yl]amino]methyl)hexanoate (HA)

To the solution of above compound IV, (S)-2-aminobutanamide hydrochloride (16.22 g, compound III), tetrabutyl ammonium bromide (8.64 g) & anhydrous sodium carbonate (28.61 g) was added under stirring at about 20° C. to about 25° C. The suspension was then stirred for about 27 h to about 30 h at about 80° C. to about 85° C. The reaction mass was cooled to about 25° C. to about 30° C. and dichloromethane and water was added to it. The reaction mass was stirred and the organic layer was separated and concentrated.

Acetone was added and the reaction mass was heated to obtain clear solution. The reaction mass was cooled to about 20-25° C. The solid obtained was filtered, washed with acetone and dried. Yield: 7.8 g; HPLC purity: >99%, Chiral purity: 96.40%, S,S-isomer 3.6%

Example 15: Preparation of (1R,2S,5R)-5-methyl-2-(propan-2-yl)cyclohexyl (3R)-3-({[(2S)-1-amino-1-oxobutan-2-yl]amino]methyl)hexanoate (IIA)

To the solid of Example 14, acetone (5.46 mL) was added and the reaction mass was heated to get clear solution. The reaction mass was cooled to about 20° C. to about 25° C. and further cooled to about 0-5° C. and stirred for about one hour. The solid was filtered and washed with acetone and dried at about 45° C. to about 55° C. under reduced pressure to obtain (1R,2S,5R)-5-methyl-2-(propan-2-yl)cyclohexyl-(3R)-3-({[(2S)-1-amino-1-oxobutan-2-yl]amino}methyl) hexanoate (compound IIA, 7 g) as a white solid.

HPLC purity: 99.88%, Chiral purity: 99.89%, S,S-isomer 0.11%

SOR [α]D25=−57.29° (c 1.0%, CHCl3)

Melting point: 119-119.7° C.

1H NMR (400 MHz, DMSO): δ 7.26 (b, 1H), 6.95 (b, 1H), 4.61-4.54 (m, 1H), 2.75-2.73 (m, 1H), 2.47-2.40 (m, 2H), 2.19-2.14 (dd, 2H), 1.85-1.82 (m, 3H), 1.66-1.61 (m, 3H), 1.48-1.39 (m, 4H), 1.37-1.30 (m, 5H), 1.28-1.18 (m, 3H), 1.04-0.83 (m, 12H), 0.72-0.70 (d, 3H)

Mass: M/Z=369.29 (M+H)

XPRD: 2 theta value 4.13, 8.20, 12.28, 18.16, 20.48, and 24.62.

13C NMR (400 MHz, CDCl$_3$): C1-10.30, C2-14.22, C3-16.19, C4-19.92, C5-20.74, C6-22.01, C7-23.27, C8-26.20, C9-26.40, C10-31.35, C11-34.19, C12-34.57, C13-35.87, C14-37.94, C15-40.89, C16-46.92, C17-52.32, C18-64.60, C19-74.20, C20-172.83, C21-177.70

IR: 3265.33, 2958.98, 2867.87, 1728.45, 1678.29, 1560.07, 1426.38, 1059.39, 726.58 cm-1

Example 16: Preparation of (2S)-2-[(4R)-2-oxo-4-propylpyrrolidin-1-yl]butanamide, Brivaracetam (I)

A mixture of compound IIA (10 g), n-heptane (150 mL) and acetic acid (4.89 g) was stirred for about 4 h to about 5 h at about 85° C. to about 90° C. The reaction mass was cooled to about 20° C. to about 30° C. and water was added to it. The reaction mass was stirred for about 15 min to about 20 min and the two layers were separated. To the aqueous layer was added sodium chloride which was stirred for 10 to 15 minutes. Ethyl acetate was added to the reaction mass and was stirred for 10-15 minutes. The two layers were separated and the organic layer was washed with sodium bicarbonate solution to adjust pH between 6-8. The organic layer was washed with brine solution. To the organic layer was added activated charcoal and the reaction mass was heated to 50-60° C. for one hour. The reaction mass was filtered through hyflo bed, washed with ethyl acetate and concentrated under vacuum at about 45-50° C. Diisopropyl ether was added and the reaction mass was heated to about 50-60° C. The reaction mass was cooled gradually to about 20-30° C. and then about 0-5° C. for about 2 h. The solid was filtered, washed with chilled diisopropyl ether and dried at about 45° C. to 55° C. for about 7-8 h. Yield: 5 g HPLC purity: >99.70%, Chiral purity: >99.5%, 2S,4S isomer: 0.10%, 2R,4S isomer: not detected, 2R,4R isomer: not detected 1H NMR (400 MHz, CDCl3): δ 6.38 (brs, 1H), 5.70 (brs, 1H), 4.44-4.48 (dd, 1H), 3.47-3.51 (dd, 1H), 3.02-3.06-(dd, 1H), 2.54-2.61 (dd, 1H), 2.31-2.37 (m, 1H), 2.05-2.11 (dd, 1H), 1.89-1.99 (m, 1H), 1.63-1.74 (m, 1H), 1.32-1.45 (m, 4H), 0.8-0.9 (m, 6H), Mass: M/Z=213.15 (M+H); IR: 3323.32, 2967.33, 2850.44, 1693.35, 1681.96, 1495.88, 1349.20, 1249.22, 1031.30 cm-1.

XPRD characteristic peak 2 theta value 8.94, 10.09, 15.05, 19.19, 21.64 and 25.02

Example 17: Preparation of methyl-3-formylhex-2-enoate

To a cooled solution of sodium hydride (7 g) in hexamethylphosphoramide (100 mL) was added slowly a solution of 5-hydroxy-4-propylfuran-2(5H)-one (25 g) in hexamethylphosphoramide (100 mL). The reaction mixture was stirred for about 1 h at about 0-5° C. and then methyl iodide (16.5 mL) was added to it. The reaction mixture was stirred at about 25-30° C. for about 30 min and then cooled to about 0-5° C. Water and methyl tert-butyl ether was added to the reaction mixture. The reaction mixture was stirred for about 10 mins and the two layers were separated. The organic layer was concentrated under reduced pressure and degassed. Yield: 26 g

Example 18: Preparation of methyl (2Z)-3-({[(2S)-1-amino-1-oxobutan-2-yl]imino}methyl)hex-2-enoate To a stirred solution of S-2-aminobutyramide HCl (22.32 g) in isopropyl alcohol (100 mL), was added triethylamine (18.15 g) at about 25-30° C. The reaction mixture was stirred for about 15 mins at about the same temperature. Methyl-3-formylhex-2-enoate (25 g) in isopropyl alcohol (25 mL) was added slowly to the reaction mixture. The reaction mixture was stirred for about 90 mins and ethyl acetate was added to it. The two layers were separated and the organic layer was concentrated under reduced pressure. Yield: 31.2 g

Example 19: Preparation of methyl 3-({[(2S)-1-amino-1-oxobutan-2-yl]amino}methyl)hexanoate A mixture of methyl (2Z)-3-({[(2S)-1-amino-1-oxobutan-2-yl]imino}methyl)hex-2-enoate (30 g) in methanol (300 mL) was hydrogenated in an autoclave using 20% Pd—C (1.5 g) by maintaining 2 kg hydrogen gas pressure. The reaction mixture was filtered through hyflo bed and washed with methanol. The filtrate was concentrated under reduced pressure. Yield: 30 g

Example 20: Preparation of (1R,2S,5R)-5-methyl-2-(propan-2-yl)cyclohexyl 3-({[(2S)-1-amino-1-oxobutan-2-yl]amino]methyl)hexanoate (II)

A mixture of methyl 3-({[(2S)-1-amino-1-oxobutan-2-yl]amino}methyl)hexanoate (25 g), L-menthol (16 g) and catalytic dimethylaminopyridine in n-heptane (250 mL) was heated azeotropically to remove methanol. The compound II was obtained as residue.

Example 20: Preparation of 2-(2-hydroxy-5-oxo-3-propyl-2,5-dihydro-1H-pyrrol-1-yl)butanamide To a mixture of 5-hydroxy-4-propylfuran-2(5H)-one (10 g) and S-2-aminobutyramide HCl (8.87 g) in toluene (100 mL) was added triethylamine (16.15 g) and the reaction mixture was stirred for about 2 h. The reaction mixture was filtered and the filtrate was concentrated under reduced pressure. Yield: 12 g

Example 21: Preparation of 3-({[(2S)-1-amino-1-oxobutan-2-yl]amino}methyl) hexanoic Acid A mixture of 2-(2-hydroxy-5-oxo-3-propyl-2,5-dihydro-1H-pyrrol-1-yl)butanamide (11 g) in methanol (100 mL) was hydrogenated in an autoclave using Pd—C (0.55 g) by maintaining 15-20 kg hydrogen gas pressure for about 6 h at about 25-30° C. The reaction mixture was filtered through hyflo bed and washed with methanol. The filtrate was concentrated under reduced pressure. Yield: 11 g

Example 22: Preparation of (1R,2S,5R)-5-methyl-2-(propan-2-yl)cyclohexyl 3-({[(2S)-1-amino-1-oxobutan-2-yl]amino]methyl)hexanoate (II)

A mixture of 3-({[(2S)-1-amino-1-oxobutan-2-yl]amino}methyl) hexanoic acid (25 g) and L-menthol (17 g) in dichloromethane (250 mL) was stirred for about 30 mins at about 25-30° C. Thionyl chloride (14.2 g) was drop wise added to it at about 25-30° C. The reaction mixture was heated. After completion of reaction, the reaction mixture was concentrated. The compound II was obtained as residue.

The invention claimed is:

1. A process for the preparation of brivaracetam, a compound of formula I, or a salt thereof,

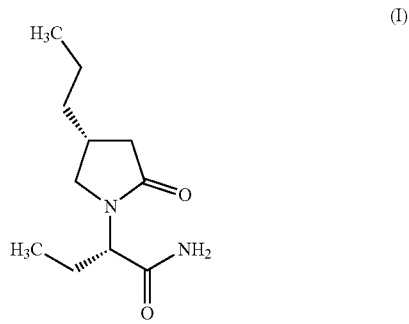

(I)

the process comprising:
i) reacting a compound of formula VI with L-menthol to obtain a compound of formula IV,

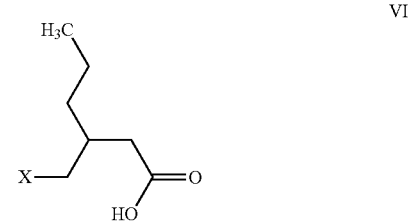

VI

-continued

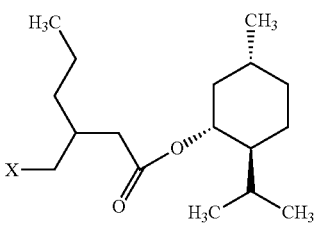
IV wherein X=Cl, Br, I, OMs or OTs;
ii) reacting the compound of formula IV with (2S)-2-aminobutanamide, a compound of formula III, to obtain a diastereomeric mixture, a compound of formula II;

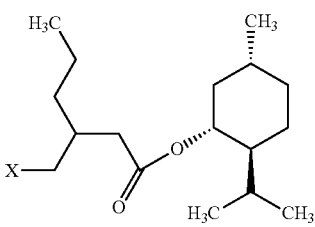
IV

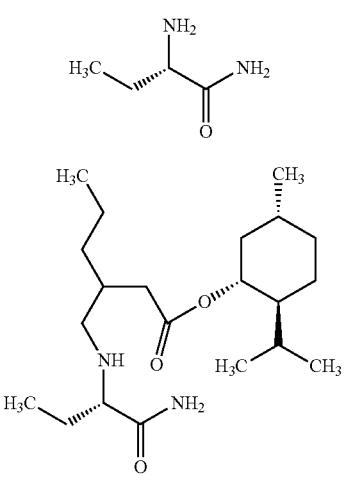
III

II

IIA iii) separating the desired diastereomer, a compound of formula IIA and the undesired diastereomer, a compound of formula IIB, from the diastereomeric mixture, the compound of formula II; and

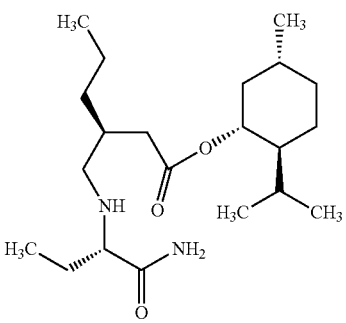
IIB iv) cyclizing the compound of formula IIA, to obtain brivaracetam, the compound of formula I.

2. The process of claim 1, wherein the reaction of the compound of formula VI with L-menthol is carried out in the presence of a coupling reagent selected from the group consisting of thionyl chloride, a carbodiimide, a 1-hydroxybenzotriazole based or 1-hydroxy-7-azabenzotriazole based phosphonium and uronium salt, a sulfinyl halide and a phosphorus halide.

3. The process of claim 2, wherein a compound of formula V,

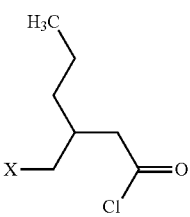
V wherein X=Cl, Br, I, OMs or OTs, is formed as an intermediate in the reaction of the compound of formula VI with L-menthol in the presence of a coupling reagent, wherein the coupling reagent is thionyl chloride.

4. The process of claim 1, wherein in step 'iii', the separation of desired diastereomer, the compound of formula IIA, and the undesired diastereomer, the compound of formula IIB, from the diastereomeric mixture, the compound of formula II, is carried out by any of the following:
x) treating the diastereomeric mixture, the compound of formula II, with a solvent in which one of the diastereomers is soluble and other diastereomer is insoluble and precipitated out; or
y) treating the diastereomeric mixture, the compound of formula II, with a solvent and adding an anti-solvent to it in which one of the diastereomers is soluble and other diastereomer is insoluble and precipitated out.

5. The process of claim 4, wherein the solvent used in 'x' is selected from the group consisting of a C1-C6 aliphatic ester and a C1-6 aliphatic ketone.

6. The process of claim 4, wherein the solvent used in 'y', is such that the diastereomeric mixture, the compound of formula II, is soluble in it, and is selected from the group consisting of a C1-C6 alcohol, a C1-C6 haloalkane and an ether.

7. The process of claim 4, wherein the anti-solvent is selected from the group consisting of a hydrocarbon, a C1-C6 aliphatic ester and a nitrile.

8. The process of claim 1, wherein the compound of formula IIA is obtained in step 'iii', wherein the content of the compound of formula IIB is less than 1% with respect to the compound of formula IIA, as determined by HPLC.

9. The process of claim 1, wherein cyclization of the compound of formula IIA, in step 'iv' is carried out in the presence of an acid.

10. The process of claim 1, wherein cyclization of the compound of formula IIA, in step 'iv' is carried out in the presence of a base.

11. The process of claim 1, wherein brivaracetam, the compound of formula I, is obtained in a diastereoisomeric excess of at least 98%, as determined by HPLC.

12. A compound of any one of formula II, formula IIA and formula IV,

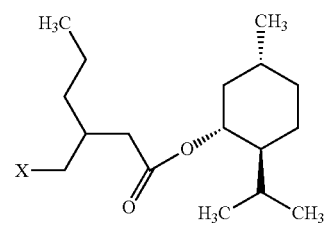
IV

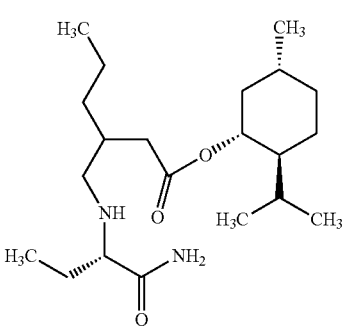
II

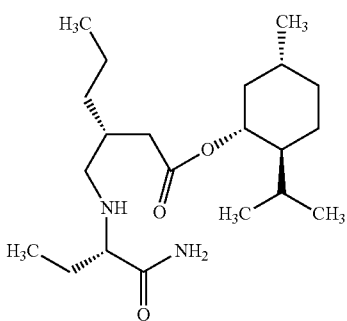
IIA wherein X=Cl, Br, I, OMs or OTs.

13. A process for the preparation of brivaracetam, a compound of formula I, or a salt thereof,

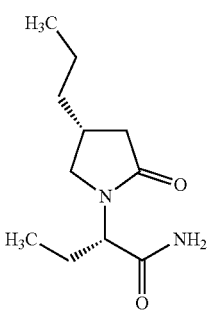
I the process comprising:
(a) obtaining a diastereomeric mixture, a compound of formula II,

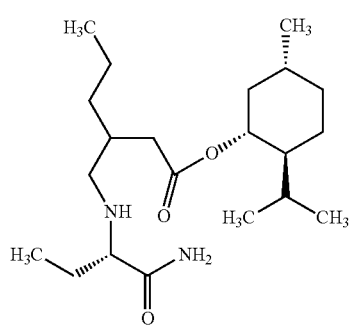
II by any one of the following:
(i) reacting the compound of formula IV wherein X=Cl, Br, I, OMs or OTs, with (2S)-2-aminobutanamide, and a compound of formula III,

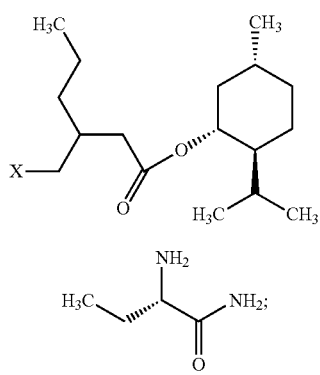
IV

III or
(ii) reacting a compound of formula VIII with L-menthol,

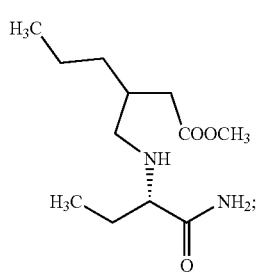

VIII or (iii) reacting a compound of formula IX with L-menthol,

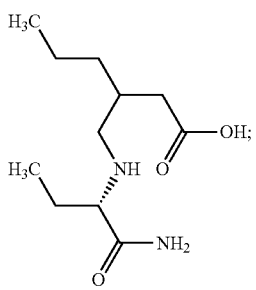

IX or (iv) reducing a compound of formula X,

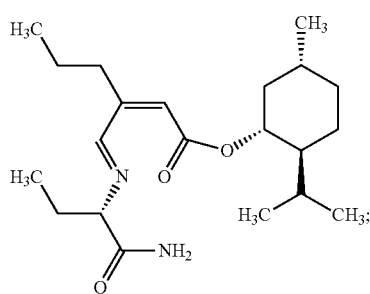

X (b) separating the desired diastereomer, a compound of formula IIA and the undesired diastereomer, a compound of formula IIB, from the diastereomeric mixture, the compound of formula II; and

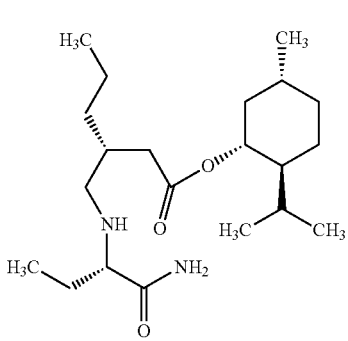

IIA

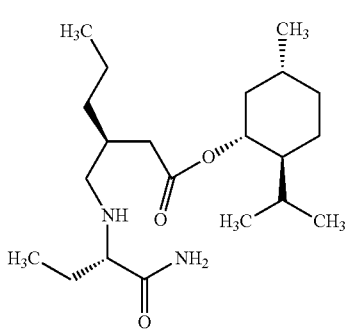

IIB (c) cyclizing the compound of formula IIA, to obtain brivaracetam, the compound of formula I.

14. The process of claim 13, wherein the reaction of the compound of formula VIII with L-menthol is carried out in the presence of a catalyst.

15. The process of claim 14, wherein the catalyst is dimethylaminopyridine.

16. The process of claim 13, wherein the reaction of the compound of formula IX with L-menthol is carried out in the presence of a coupling reagent.

17. The process of claim 16, wherein the coupling reagent is selected from the group consisting of thionyl chloride, a carbodiimide, a 1-hydroxybenzotriazole based or 1-hydroxy-7-azabenzotriazole based phosphonium and uronium salt, a sulfinyl halide and a phosphorus halide.

18. The process of claim 13, wherein the compound of formula X is reduced using a hydrogen source in the presence a metal catalyst.

19. The process of claim 18, wherein the hydrogen source is selected from the group consisting of hydrogen gas, formic acid, isopropanol, and dihydroanthracene.

20. The process of claim 18, wherein the metal catalyst is selected from the group consisting of nickel, palladium, platinum, ruthenium, rhodium and iridium.

* * * * *